US008871207B2

(12) United States Patent
Lanzavecchia

(10) Patent No.: US 8,871,207 B2
(45) Date of Patent: Oct. 28, 2014

(54) NEUTRALIZING ANTI-INFLUENZA A VIRUS ANTIBODIES AND USES THEREOF

(75) Inventor: Antonio Lanzavecchia, Porza (CH)

(73) Assignee: Humabs, LLC, San Francisco, CA (US)

( * ) Notice: Subject to any disclaimer, the term of this patent is extended or adjusted under 35 U.S.C. 154(b) by 168 days.

(21) Appl. No.: 13/185,157

(22) Filed: Jul. 18, 2011

(65) Prior Publication Data

US 2011/0274702 A1 Nov. 10, 2011

Related U.S. Application Data

(63) Continuation-in-part of application No. 12/509,731, filed on Jul. 27, 2009.

(60) Provisional application No. 61/083,838, filed on Jul. 25, 2008, provisional application No. 61/181,582, filed on May 27, 2009.

(51) Int. Cl.
| | |
|---|---|
| A61K 39/42 | (2006.01) |
| C07K 16/10 | (2006.01) |
| C12N 15/13 | (2006.01) |
| C12N 5/10 | (2006.01) |
| A61K 39/00 | (2006.01) |

(52) U.S. Cl.
CPC ......... *C07K 16/1018* (2013.01); *C07K 2317/34* (2013.01); *C07K 2317/76* (2013.01); *C07K 2317/56* (2013.01); *A61K 2039/505* (2013.01); *C07K 2299/00* (2013.01); *C07K 2317/565* (2013.01)
USPC .................. 424/147.1; 530/388.3; 536/23.53; 435/339; 435/320.1

(58) Field of Classification Search
None
See application file for complete search history.

(56) References Cited

U.S. PATENT DOCUMENTS

| | | | |
|---|---|---|---|
| 3,766,162 | A | 10/1973 | Spector |
| 3,791,932 | A | 2/1974 | Schuurs et al. |
| 3,817,837 | A | 6/1974 | Rubenstein |
| 4,179,337 | A | 12/1979 | Davis |
| 4,233,402 | A | 11/1980 | Maggio et al. |
| 4,495,285 | A | 1/1985 | Shimizu |
| 4,609,546 | A | 9/1986 | Hiratani |
| 4,676,980 | A | 6/1987 | Segal |
| 4,766,106 | A | 8/1988 | Katre et al. |
| 4,831,175 | A | 5/1989 | Gansow |
| 5,595,721 | A | 1/1997 | Kaminski et al. |
| 5,807,715 | A | 9/1998 | Morrison et al. |
| 6,300,064 | B1 | 10/2001 | Knappik et al. |
| 6,300,104 | B1 | 10/2001 | Morrison et al. |

FOREIGN PATENT DOCUMENTS

| | | |
|---|---|---|
| EP | 1264885 | 12/2002 |
| EP | 1666059 | 6/2006 |
| EP | 1925318 | 5/2008 |
| EP | 1983047 | 10/2008 |
| WO | 0052031 | 9/2000 |
| WO | 0052473 | 9/2000 |
| WO | 2004076677 | 10/2004 |
| WO | WO-2005014038 | 2/2005 |
| WO | 2006124269 | 11/2006 |
| WO | 2007045477 | 4/2007 |
| WO | WO-2007/091624 | 8/2007 |
| WO | 2007134327 | 11/2007 |
| WO | 2008028946 | 3/2008 |
| WO | 2008054606 | 5/2008 |
| WO | 2008066691 | 6/2008 |
| WO | 2008076379 | 6/2008 |
| WO | 2008084410 | 7/2008 |
| WO | 2008110937 | 9/2008 |
| WO | WO-2010010466 | 1/2010 |

OTHER PUBLICATIONS

Варечкова et al., Virus Research, vol. 132, Issues 1-2, Mar. 2008, pp. 181-186, (epub. Nov. 26, 2007).*
Cafiso et al., "Preparation of unilamellar lipid vesicles at 37° C. by vaporization methods," Biochimica et Biophysica Acta (BBA)—Biomembranes 1981, 649:129-132.
Cho et al., "An oriP expression vector containing the HIV-1 Tat/TAR transactivation axis produces high levels of protein expression in mammalian cells," Cytotechnology 2001, 37:23-30.
Cho et al., "Versatile Expression System for Rapid and Stable Production of Recombinant Proteins," Biotechnol Prog 2003, 19:229-232.
Ekiert et al., (2009). "Antibody Recognition of a Highly Conserved Influenza Virus Epitope," Science 324:246-251.
Gabizon et al., (1982). "Liposomes as in Vivo Carriers of Adriamycin: Reduced Cardiac Uptake and Preserved Antitumor Activity in Mice," Cancer Research 42: 4734-4739.
Gerhard et al., (2006). "Prospects for Universal Influenza Virus Vaccine," Emerging Infectious Diseases 12:569-574.
Gioia et al., (2008) "Cross-subtype Immunity Against Avian Influenza in Persons Recently Vaccinated for Influenza," Emerging Infectious Diseases 14:121-128.
Holt et al., "Domain antibodies: proteins for therapy," Trends in Biotechnology 2003, 21(11):484-490.

(Continued)

*Primary Examiner* — Mary E Mosher
*Assistant Examiner* — Myron Hill
(74) *Attorney, Agent, or Firm* — Glance Law Group

(57) ABSTRACT

The invention relates to antibodies, and antigen binding fragments thereof, that specifically bind to an epitope in the stem region of an influenza A hemagglutinin trimer and neutralize a group 1 subtype and a group 2 subtype of influenza A virus. The invention also relates to nucleic acids that encode, immortalized B cells and cultured single plasma cells that produce, and to epitopes that bind to such antibodies and antibody fragments. In addition, the invention relates to the use of the antibodies, antibody fragments, and epitopes in screening methods as well as in the diagnosis, treatment and prevention of influenza A virus infection.

11 Claims, 10 Drawing Sheets

(56) References Cited

OTHER PUBLICATIONS

Jones et al., "High-Level Expression of Recombinant IgG in the Human Cell Line PER.C6," Biotechnol Prog 2003, 19(1):163-168.
Kashyap et al., (2008). "Combinatorial antibody libraries from survivors of the Turkish H5N1 avian influenza outbreak reveal virus neutralization strategies," Proc. Natl. Acad. Sci. USA 105:5986-5991.
Kohler, G. and Milstein, C,. 1975,Continuous cultures of fused cells secreting antibody of predefined specificity, Nature 256:495-497.
Kozbor et al., 1983, "The production of monoclonal antibodies from human lymphocytes," Immunology Today 4:72-79.
Little et al., "Of mice and men: hybridoma and recombinant antibodies," Immunology Today 2000, 21(8):364-370.
Okuno et al., (1993). "A Common Neutralizing Epitope Conserved between the Hemagglutinins of Influenza A Virus Hi and H2 Strains," Journal of Virology 67:2552-2558.
Prabhu et al., (2009). "Monoclonal Antibodies against the Fusion Peptide of Hemagglutinin Protect Mice from Lethal Influenza A Virus H5N1 Infection," Journal of Virology 83:2553-2562.
Poznansky M. and Juliano R. L. (1984) "Biological Approaches to the Controlled Delivery of Drugs: A Critical Review," Pharm Revs 36:277-336.
Rowe et al., (1999). "Detection of Antibody to Avian Influenza A (H5N1) Virus in Human Serum by Using a Combination of Serologic Assays," J Clin Microbiol 37(4):937-943.
Simmons C. P. et al., (2007) Prophylactic and Therapeutic Efficacy of Human Monoclonal Antibodies against H5N1 Influenza. PLoS Medicine vol. 4: issue 5; pp. 928-936.
Smirnov et al., (1999). "An Epitope Shared by the Hemagglutinins of H1, H2, H5, and H6 Subtypes of influenza A Virus," Acta Virol 43:237-244.
Smirnov et al., (2000). "Prevention and treatment of bronchopneumonia in mice caused by mouse-adapted variant of avian H5N2 influenza A virus using monoclonal antibody against conserved epitope in the HA stem region," Arch Virol 145:1733-1741.
Sui et al., (2009). "Structural and functional bases for broad-spectrum neutralization of avian and human influenza A viruses," Nature Structural & Molecular Biology 16:265-273.
Szoka F Jr. and Papahadjopoulos D. (1980) "Comparative Properties and Methods of Preparation of Lipid Vesicles (Liposomes)," Ann. Rev. Biophys. Bioeng. 9:467-508.
Temperton, et al., (2005). "Longitudinally Profiling Neutralizing Antibody Response to SARS Coronavirus with Pseudotypes," Emerg Infect Dis 11:411-416.
Throsby et al., (2008). "Heterosubtypic Neutralizing Monoclonal Antibodies Cross-Protective against H5N1 and H1N1 Recovered from Human IgM+ Memory B Cells," PLoS One vol. 3, Issue 12, pp. 1-15.
Traggiai et al., (2004). "Heterosubtypic Neutralizing Monoclonal Antibodies Cross-Protective against H5N1 and H1N1 Recovered from Human IgM+ Memory B Cells," Nat Med 10:871-875.
Wrammert et al., (2008). "Rapid cloning of high-affinity human monoclonal antibodies against influenza virus," Nature 453:667-671.
Written Opinion of the International Searching Authority received in International Application No. PCT/IB2009/006616, 2010.
Written Opinion of the International Searching Authority received in International Application No. PCT/IB2009/006623, 2010.
Yoshida et al., (2009). "Cross-Protective Potential of a Novel Monoclonal Antibody Directed against Antigenic Site B of the Hemagglutinin of Influenza A Viruses," PLoS Pathogens vol. 5, Issue 3, pp. 1-9.
Ziegler et al., "Type- and Subtype-Specific Detection of Influenza Viruses in Clinical Specimens by Rapid Culture Assay," Journal of Clinical Microbiology,1995, 33:318-321.
Borrebaeck, et al., "Kinetic Analysis of Recombinant Antibody-Antigen Interaction: Relation Between Structural Domains and Antigen Binding", Nature Biotechnology. 10(6), (1992),697-698.
Bresson, et al., "Safety and Immunogenicity of an Inactivated Split-Virion Influenza A/Vietnam/1194/2004 (H5N1) Vaccine: Phase I Randomised Trial", Lancet 2006; 367, (May 11, 2006),1657-1664.
Casset, et al., "A Peptide Mimetic of an Anti-CD4 Monoclonal Antibody by Rational Design", Biochemical and Biophysical Research Communications 307, (2003),198-205.
Colman, "Effects of Amino Acid Sequence Changes on Antibody-Antigen interactions", Res. Immunol. 145, (1994),33-36.
Corbeil, et al., "Involvement of the Complement System in the Protection of Mice from Challenge with Repiratory Syncytial Virus Long Strain Following Passive Immunization With Monoclonal Antibody 18A2B2", Vaccine, vol. 14, No. 6, (1996),521-525.
Corti, et al., "Heterosubtypic Neutralizing Antibodies are Produced by Individuals Immunized With a Seasonal Influenza Vaccine", The Journal of Clinical Investigation, vol. 120, No. 5, (May 2010),1663-1673.
Davies, et al., "Affinity Improvement of Single Antibody VH Domains: Residues in All Three Hypervariable Regions Affect Antigen Binding", Immunotechnology 2, (1996),169-179.
Goldsby, et al., "Kuby Immunology", Kuby Immunology (4th Edition), Chapter 4, (2000),1-34.
Kaverin, et al., "Epitope Mapping of the Hemagglutinin Molecule of a Highly Pathogenic H5N1 Influenza Virus by Using Monoclonal Antibodies", Journal of Virology, vol. 81, No. 23, (Dec. 2007),12911-12917.
Mitchell, et al., "Induction of HeteroSubtypic Immunity to Influenza A Virus Using a DNA Vaccine Expressing Hemagglutinin-C3d Fusion Proteins", Vaccine 21, (2003),902-914.
Nguyen, et al., "Heterosubtypic Immunity to Influenza A Virus Infection Requires B Cells but Not CD8+ Cytotoxic T Lymphocytes", The Journal of infectious Diseases 183, (2001),368-376.
Ohno, et al., "Antigen-Binding Specificities of Antibodies Are Primarily Determined by Seven Residues of V H", proc. Natl. Acad. Sci. vol. 82, (May 1985),2945-2949.
Paul, "Fundamental Immunology", Fundamental Immunology. 3rd Edition, Chapters 8 and 9 (excerpts), (1993),242 and 292-295.
Poznansky, et al., "Bilogical Macromolecules as Carriers of Drugs and Enzymes", Drug Delivery Systems (R.L. Juliano, ed. Oxford, NY), (1980),253-315.
Rudikoff, et al., "Single Amino Acid Substitution Altering Antigen-Binding Specificity", Proc. Natl. Acad. Sci. vol. 79, (Mar. 1982),1979-1983.

* cited by examiner

FI6-variant 3 VH QVQLVESGGGVVQPGRSLRLSCAAS**MHWVRQAPGKGLEWVAV**YYADSV
(SEQ ID NO:55)                             (SEQ ID NO:1)                    (SEQ ID NO:41)

FI6-variant 3 VH KGRFTISRDNSKNTLYLQMNSLRAEDTAVYC****WGQGTLVTVSS
(SEQ ID NO:55)                                           (SEQ ID NO: 42)

FI6-variant 3 VK DIVMTQSPDSLAVSLGERATINCKSS**LAWYQQKPGQPPKLLIY**TRESGVPDR
(SEQ ID NO:57)                             (SEQ ID NO:4)                    (SEQ ID NO:5)

FI6-variant 3 VK FSGSGSGTDFTLTISSLQAEDVAVYYC****FGQGTKVEIK
(SEQ ID NO:57)                             (SEQ ID NO: 6)

Fig. 7

NEUTRALIZING ANTI-INFLUENZA A VIRUS ANTIBODIES AND USES THEREOF

This application claims the benefit of priority of U.S. provisional Application Nos. 61/083,838 and 61/181,582, filed Jul. 25, 2008, and May 27, 2009, respectively, and U.S. application Ser. No. 12/509,731, filed Jul. 27, 2009, the disclosures of which, along with all documents cited therein, are hereby incorporated by reference in their entirety, as if written herein.

BACKGROUND

The neutralizing antibody response to Influenza A virus is typically specific for a given viral subtype. There are 16 influenza A subtypes defined by their hemagglutinin ("HA") proteins. The 16 HAs, H1-H16, can be classified into two groups. Group 1 consists of H1, H2, H5, H6, H8, H9, H11, H12, H13, and H16 subtypes, and group 2 includes H3, H4, H7, H10, H14 and H15 subtypes. While all subtypes are present in birds, mostly H1, H2 and H3 subtypes cause disease in humans. H5, H7 and H9 subtypes are causing sporadic severe infections in humans and may generate a new pandemic. H1 and H3 viruses continuously evolve generating new variants, a phenomenon called antigenic drift. As a consequence, antibodies produced in response to past viruses are poorly- or non-protective against new drifted viruses. A consequence is that a new vaccine has to be produced every year against H1 and H3 viruses that are predicted to emerge, a process that is very costly as well as not always efficient. The same applies to the production of a H5 influenza vaccine. Indeed it is not clear whether the current H5 vaccines based on the Vietnam or Indonesia influenza A virus isolates will protect against a future pandemic H5 virus.

For these reasons it would be highly desirable to have a vaccine that induces broadly neutralizing antibodies capable of neutralizing all influenza A virus subtypes as well as their yearly variants (reviewed by Gerhard et al., 2006). In addition broadly neutralizing heterosubtypic antibodies could be administered as medicaments for prevention or therapy of influenza A infection. For the manufacture of such medicaments it is important to select antibodies that are produced at high titers to reduce costs of production.

Antibodies that recognize influenza A virus have been characterized. Antibodies to M2, an invariant small protein expressed on infected cells but not on infectious viruses, have shown some protective effect in vivo, possibly by targeting infected cells for destruction by NK cells or cytotoxic T cells. It is also possible to target the HA protein with neutralizing antibodies. HA is synthesized as a homo-trimeric precursor polypeptide HA0. Each monomer can be independently cleaved post-translationally to form two polypeptides, HA1 and HA2, linked by a single disulphide bond. The larger N-terminal fragment (HAL 320-330 amino acids) forms a membrane-distal globular domain that contains the receptor-binding site and most determinants recognized by virus-neutralizing antibodies. The HA1 polypeptide of HA is responsible for the attachment of virus to the cell surface. The smaller C-terminal portion (HA2, ≈180 amino acids) forms a stem-like structure that anchors the globular domain to the cellular or viral membrane. The HA2 polypeptide mediates the fusion of viral and cell membranes in endosomes, allowing the release of the ribonucleoprotein complex into the cytoplasm.

The degree of sequence homology between subtypes is smaller in the HA1 polypeptides (34%-59% homology between subtypes) than in the HA2 polypeptide (51%-80% homology). The most conserved region is the sequence around the cleavage site, particularly the HA2 N-terminal 11 amino acids, termed fusion peptide, which are conserved among all influenza A virus subtypes. Part of this region is exposed as a surface loop in the HA precursor molecule (HA0), but becomes inaccessible when HA0 is cleaved into HA1/HA2. In summary there are conserved regions among different HA subtypes especially in the HA1-HA2 joining region and in the HA2 region. However these regions may be poorly accessible to neutralizing antibodies.

There has only been limited success in identifying antibodies that neutralize more than one subtype of influenza A virus. Further, the breath of neutralization of antibodies identified thus far is narrow and their potency is low. Okuno et al, immunized mice with influenza virus A/Okuda/57 (H2N2) and isolated a monoclonal antibody (C179) that binds to a conserved conformational epitope in HA2 and neutralizes the Group 1 H2, H1 and H5 subtype influenza A viruses in vitro and in vivo in animal models (Okuno et al., 1993; Smirnov et al., 1999; Smirnov et al., 2000).

Gioia et al., described the presence of H5N1 virus neutralizing antibodies in the serum of some individuals that received a conventional seasonal influenza vaccine (Gioia et al., 2008). The authors suggest that the neutralizing activity might be due to antibodies to neuraminidase (N1). However, monoclonal antibodies were not isolated and target epitopes were not characterized. Also, it is not clear whether the serum antibodies neutralize other subtypes of influenza A virus.

Heterosubtypic human antibodies that bind to an epitope in the stem-like region of HA, and capable of neutralizing some influenza A virus subtypes within either Group 1 or Group 2, have been isolated from memory B cells and plasma cells of immune donors. However, Influenza A-specific neutralizing antibodies targeting epitopes in the HA trimer conserved on all 16 subtypes and capable of neutralizing viruses of both Group 1 and Group 2 subtypes have not been found so far, and their isolation remains a major goal for therapeutic approaches and vaccine design.

Despite decades of research, there are no marketed antibodies that broadly neutralize or inhibit influenza A virus infection or attenuate disease caused by influenza A virus. Therefore, there is a need to identify new antibodies that neutralize multiple subtypes of influenza A virus and can be used as medicaments for prevention or therapy of influenza A infection. There is a further need to identify antibodies that are produced at high titers to reduce costs of production.

SUMMARY

The invention is based, in part, on the isolation from individuals vaccinated with the seasonal influenza vaccine of naturally occurring human monoclonal antibodies that bind to HA and neutralize infection of more than one subtype of influenza A virus, as well as novel epitopes to which the antibodies of the invention bind. Accordingly, in one aspect of the invention, the invention comprises an antibody and antigen binding fragments thereof that neutralize infection of more than one subtype of influenza A virus, selected from group 1 and group 2 subtypes.

In one embodiment of the invention, the invention comprises an isolated antibody, or an antigen binding fragment thereof, that neutralizes infection of a group 1 subtype and a group 2 subtype of influenza A virus. In another embodiment of the invention, it comprises an isolated antibody, or an antigen-binding fragment thereof, that neutralizes infection of a group 1 subtype and a group 2 subtype of influenza A virus and specifically binds to an epitope in the stem region of an influenza A hemagglutinin (HA) trimer, wherein the heavy and light chain of the antibody, or antigen binding fragment thereof, contact amino acids in a first, proximal monomer and a second, distal, right monomer of the HA trimer.

In yet another embodiment of the invention, the invention comprises an isolated antibody, or an antigen-binding fragment thereof, that neutralizes infection of a group 1 subtype and a group 2 subtype of influenza A virus and specifically binds to an epitope in the stem region of an influenza A HA trimer, wherein the heavy and light chain of the antibody, or antigen binding fragment thereof, contact amino acids in a first, proximal monomer and a second, distal, right monomer of the HA trimer, and wherein the antibody, or antigen-binding fragment thereof, is produced in transfected cells at titers of at least 3 fold higher than the titer at which FI6 variant 2 is produced.

In still another embodiment of the invention, the invention comprises an isolated antibody, or an antigen-binding fragment thereof, that neutralizes infection of a group 1 subtype and a group 2 subtype of influenza A virus and specifically binds to an epitope in the stem region of an influenza A HA trimer, wherein the heavy and light chain of the antibody, or antigen binding fragment thereof, contact amino acids in a first, proximal monomer and a second, distal, right monomer of the HA trimer, and wherein the antibody, or antigen-binding fragment thereof, comprises: (i) the heavy chain CDR1, CDR2 and CDR3 sequences as set forth in SEQ ID NOs: 1, 41 and 43, respectively, or as set forth in SEQ ID NOs: 1, 41 and 42, respectively; and (ii) the light chain CDR1, CDR2, and CDR3 sequences as set forth in SEQ ID NOs: 4, 5 and 6, respectively, or as set forth in SEQ ID NOs: 44, 5 and 6, respectively.

In another embodiment of the invention, the invention comprises an isolated antibody, or an antigen binding fragment thereof, comprising at least one complementarity determining region (CDR) sequence having at least 95% sequence identity to any one of SEQ ID NOs: 1-6, 17-22, or 41-44, wherein the antibody neutralizes influenza A virus.

In another embodiment of the invention, it comprises an isolated antibody, or an antigen-binding fragment thereof, that neutralizes infection of a group 1 subtype and a group 2 subtype of influenza A virus and comprises: (i) the heavy chain CDR1, CDR2 and CDR3 sequences as set forth in SEQ ID NOs: 1, 41 and 43, respectively, or as set forth in SEQ ID NOs: 1, 41 and 42, respectively; and (ii) the light chain CDR1, CDR2, and CDR3 sequences as set forth in SEQ ID NOs: 4, 5 and 6, respectively, or as set forth in SEQ ID NOs: 44, 5 and 6, respectively.

In yet another embodiment of the invention, the invention comprises an isolated antibody, or an antigen binding fragment thereof, comprising a heavy chain CDR1 with the amino acid sequence of SEQ ID NO: 1 or SEQ ID NO: 17; a heavy chain CDR2 with the amino acid sequence of SEQ ID NO: 2, SEQ ID NO: 18, or SEQ ID NO: 41; and a heavy chain CDR3 with the amino acid sequence of SEQ ID NO: 3, SEQ ID NO: 19, SEQ ID NO: 42 or SEQ ID NO: 43, wherein the antibody neutralizes influenza A virus. In yet another embodiment of the invention, it comprises an isolated antibody, or an antigen binding fragment thereof, comprising a light chain CDR1 with the amino acid sequence of SEQ ID NO: 4, SEQ ID NO: 20 or SEQ ID NO: 44; a light chain CDR2 with the amino acid sequence of SEQ ID NO: 5 or SEQ ID NO: 21; and a light chain CDR3 with the amino acid sequence of SEQ ID NO: 6 or SEQ ID NO: 22, wherein the antibody neutralizes influenza A virus.

In still another embodiment of the invention, the invention comprises an isolated antibody, or an antigen binding fragment thereof, wherein the antibody comprises a heavy chain variable region comprising the amino acid sequence of SEQ ID NO: 13 and a light chain variable region comprising the amino acid sequence of SEQ ID NO: 14; or a heavy chain variable region comprising the amino acid sequence of SEQ ID NO: 33 and a light chain variable region comprising the amino acid sequence of SEQ ID NO: 14; or a heavy chain variable region comprising the amino acid sequence of SEQ ID NO: 29 and a light chain variable region comprising the amino acid sequence of SEQ ID NO: 30; or a heavy chain variable region comprising the amino acid sequence of SEQ ID NO: 35 and a light chain variable region comprising the amino acid sequence of SEQ ID NO: 30; or a heavy chain variable region comprising the amino acid sequence of SEQ ID NO: 59 and a light chain variable region comprising the amino acid sequence of SEQ ID NO: 57; or a heavy chain variable region comprising the amino acid sequence of SEQ ID NO: 59 and a light chain variable region comprising the amino acid sequence of SEQ ID NO: 61; or a heavy chain variable region comprising the amino acid sequence of SEQ ID NO: 55 and a light chain variable region comprising the amino acid sequence of SEQ ID NO: 57; or a heavy chain variable region comprising the amino acid sequence of SEQ ID NO: 55 and a light chain variable region comprising the amino acid sequence of SEQ ID NO: 61 and wherein the antibody neutralizes a group 1 subtype and a group 2 subtype of influenza A virus. The invention further comprises an antibody, or an antigen binding fragment thereof, wherein the antibody is FI6 variant 1, FI6 variant 2, FI6 variant 3, FI6 variant 4, or FI6 variant 5.

In yet another embodiment of the invention, the invention comprises an antibody, or antigen binding fragment thereof, that neutralizes infection of a group 1 subtype and a group 2 subtype of influenza A virus, wherein the antibody or fragment thereof is expressed by an immortalized B cell clone.

In another aspect, the invention comprises a nucleic acid molecule comprising a polynucleotide encoding an antibody or antibody fragment of the invention. In yet another aspect, the invention comprises a vector comprising a nucleic acid molecule of the invention or a cell expressing an antibody of the invention or an antigen binding fragment thereof. In yet another embodiment, the invention comprises a cell comprising a vector of the invention. In still another aspect, the invention comprises an isolated or purified immunogenic polypeptide comprising an epitope that binds to an antibody or antigen binding fragment of the invention.

The invention further comprises a pharmaceutical composition comprising an antibody of the invention or an antigen binding fragment thereof, a nucleic acid molecule of the invention, a vector comprising a nucleic acid molecule of the invention, a cell expressing an antibody or an antibody fragment of the invention, a cell comprising a vector of the invention, or an immunogenic polypeptide of the invention, and a pharmaceutically acceptable diluent or carrier. The invention also comprises a pharmaceutical composition comprising a first antibody or an antigen binding fragment thereof, and a second antibody, or an antigen binding fragment thereof, wherein the first antibody is an antibody of the invention, and the second antibody is any antibody, or antigen binding fragment thereof, that neutralizes influenza A or influenza B virus infection.

Use of an antibody of the invention, or an antigen binding fragment thereof, a nucleic acid of the invention, a vector comprising a nucleic acid of the invention, a cell expressing a vector of the invention, an isolated or purified immunogenic polypeptide comprising an epitope that binds to an antibody or antibody fragment of the invention, or a pharmaceutical composition of the invention (i) in the manufacture of a medicament for the treatment of influenza A virus infection, (ii) in a vaccine, or (iii) in diagnosis of influenza A virus infection is also contemplated to be within the scope of the invention. Further, use of an antibody of the invention, or an antigen binding fragment thereof, for monitoring the quality of anti-influenza A virus vaccines by checking that the antigen of said vaccine contains the specific epitope in the correct conformation is also contemplated to be within the scope of the invention.

In another aspect, the invention provides a method of preventing, treating or reducing influenza A virus infection or lowering the risk of influenza A virus infection comprising administering to a subject in need thereof, a therapeutically effective amount of an antibody or an antigen binding antibody fragment of the invention.

In a further aspect, the invention comprises an epitope which specifically binds to an antibody of the invention, or an antigen binding fragment thereof, for use (i) in therapy, (ii) in the manufacture of a medicament for treating influenza A virus infection, (iii) as a vaccine, or (iv) in screening for ligands able to neutralise influenza A virus infection.

DESCRIPTION OF FIGURES

FIG. 3A shows the trimer of H3 HA binding three FI6 variant 3 antibodies in Ribbons representation. One of the HA monomers is colored black for HA1 and dark grey for HA2, while the other two HA monomers are in light grey. FIGS. 3B and 3C show a zoom view of the interaction of the LCDR1 loop with the fusion peptide of the neighboring HA monomer in H1/FI6 variant 3 and H3/FI6 variant 3 complexes, respectively. FIGS. 3D and 3E show the structures of monomers from H5 HA in complex with CR6261 (pdb ID 2GBM) (D) and F10 (pdb 3FKU) (E) binding to a similar region compared to FI6 variant 3 but with their VH domain sitting 5-10 Å lower on the HA.

FIGS. 5A and 5B show the positioning of the carbohydrate side chain at Asn-38 in the H3 HA apo-structure (A) and in the FI6 variant 3 bound structure (B). FIGS. 5C and 5D show the orientation of HA1 Trp-21 in different antibody complexes. The C panel shows Phe-100D of the HCDR3 loop of FI6 variant 3 (referred to in the figure as FI6) interacting with the F sub-domain of the H1 or H3 HA. The D panel shows the HCDR2 loop of the F10 and CR6261 antibodies presenting Phe-55 and Phe-54 respectively, towards Trp-21 of H5 HA.

FIG. 6A: Contact footprint for FI6 variant 3/H1 uncleaved; FIG. 6B: FI6 variant 3/H3 cleaved; FIG. 6C: CR6261/H5; and FIG. 6D: F10/H5. Unlike CR6261 and F10, FI6 variant 3 makes contact with two HA monomers. For the FI6 variant 3 complexes, glycosylation sites at the antibody/HA interface are labeled.

FIG. 7 shows the residues (in bold, Kabat numbering) contacting HA in FI6 variant 3 VH and VK chains.

FIG. 8A shows survival curves and FIG. 8B shows the body weight loss of BALB/c mice (five per experimental condition) that received different doses of FI6 variant 3 i.v. three hours before intranasal infection with 10 MLD50 (50% lethal dose in mice) H1N1 A/PR/8/34 virus. FIG. 8C shows the body weight loss of mice (ten per experimental condition) that received different doses of FI6 variant 3 i.v. three hours before infection with $3 \times 10^5$ pfu of H3N2 HK-x31 virus. Shown is one representative experiment out of the three that were performed. Also shown are survival curve (FIG. 8D) and body weight loss (FIG. 8E) of mice (five per experimental condition) that received 15 mg/kg of FI6 variant 3 i.v. on day 0 (3 hours before infection) or on day 1, 2 and 3 after infection with 10 MLD50 of A/PR/8/34 virus. One representative experiment out of the two performed is shown. Shown are mean values±SD. FIGS. 8F and 8G, shows survival curves of mice (ten per experimental condition) that received 10 mg/kg (F) or 3 mg/kg (G) of FI6 variant 2 (FI6-v2), FI6-v2 KA (that lack complement binding), FI6-v2 LALA (that lack complement and FcR binding) or control antibody one day before infection with A/PR/8/34 virus.

DETAILED DESCRIPTION

Figure 1:
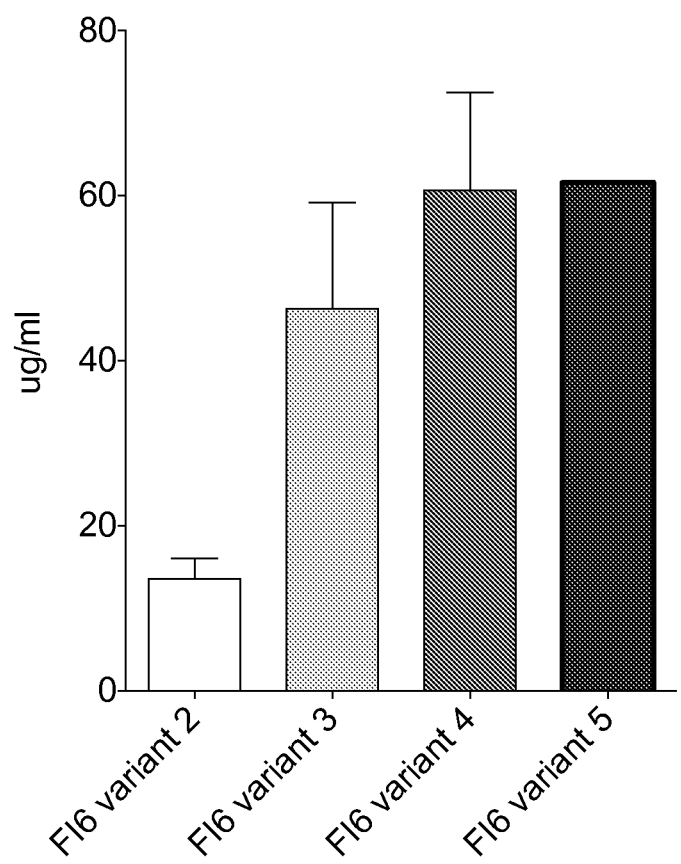
FIG. 1 shows the titers of antibody production of 293F cells transiently transfected with vectors expressing genes encoding FI6 variant 2, 3. 4 or 5.

The invention is based, in part, on the discovery and isolation, from individuals that were vaccinated with the seasonal influenza A vaccine, of naturally occurring human antibodies that broadly neutralize influenza A virus of different subtypes as well as novel epitopes to which the antibodies of the invention bind. Such antibodies are desirable, as only one or few antibodies are required in order to neutralize different subtypes of influenza A virus. Further, the broadly neutralizing heterosubtypic antibodies are produced at high titers to reduce costs of production of medicaments comprising the antibodies. In addition, the epitopes recognized by such antibodies may be part of a vaccine capable of inducing broad protection against both seasonal and candidate pandemic isolates of different subtypes.

Accordingly, in one aspect, the invention provides an isolated antibody, and antigen binding fragments thereof, that neutralize at least two influenza A viruses in group 1 and group 2 subtypes. In one embodiment, the invention provides an isolated antibody, or an antigen binding fragment thereof, that neutralizes infection of a group 1 subtype and a group 2 subtype of influenza A virus.

In another embodiment, it provides an isolated antibody, or an antigen-binding fragment thereof, that neutralizes infection of a group 1 subtype and a group 2 subtype of influenza A virus and specifically binds to an epitope in the stem region of an influenza A HA trimer, wherein the heavy and light chain of the antibody, or antigen binding fragment thereof, contact amino acids in a first, proximal monomer and a second, distal, right monomer of the HA trimer.

As discussed earlier, the HA protein is synthesized as a trimeric precursor polypeptide HA0 comprising three identical monomers (homo-trimer). Each monomer may, or may not, be cleaved independent of the other two monomers. Upon post-translational cleavage, each monomer forms two polypeptides, HA1 and HA2, which are otherwise linked by a single disulphide bond. The heavy and light chains of the antibodies of the invention contact two of the three monomers of the HA trimer. The monomers contacted by the antibodies of the invention may be cleaved, or uncleaved. For clarity purposes and for the purposes of understanding the schematic representations in the figures, we refer to the two monomers contacted by the antibodies of the invention as the proximal monomer and the distal, right monomer.

As used herein, the terms "antigen binding fragment," "fragment," and "antibody fragment" are used interchangeably to refer to any fragment of an antibody of the invention that retains the antigen-binding activity of the antibody. Examples of antibody fragments include, but are not limited to, a single chain antibody, Fab, Fab', F(ab')2, Fv or scFv. Further, the term "antibody" as used herein includes both antibodies and antigen binding fragments thereof.

As used herein, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used, alone or in combination, as prophylactic or therapeutic agents upon appropriate formulation, in association with active vaccination, as a diagnostic tool, or as a production tool as described herein.

X-ray crystallography studies of Group-1 specific heterosubtypic antibodies co-crystallized with H1 and H5 HA known in the art show that the antibodies interact with only one monomer of the HA trimer. Further, the studies show that the antibodies contact the HA with only the CDR residues of the heavy chain but not of the light chain. In contrast, the antibodies or antigen binding fragments of the invention contact, not one, but two of the three HA monomers. Additionally, the antibodies of the invention contact the HA with CDR residues from both the heavy chain and the light chain. In addition, the nature of the interactions made by antibodies or antigen binding fragments of the invention with the HA are markedly different to those made by the other antibodies, CR6261 and F10. The most striking difference is that the interaction of the antibodies of the invention with the hydrophobic groove on HA is mediated solely by CDR3 of the heavy chain (HCDR3), whereas for CR6261 and F10 all three HCDRs are involved in the binding.

In one embodiment, the heavy chains of the antibodies or antigen binding fragments of the invention contact amino acid residues in the proximal monomer, and the light chains of the antibodies or antigen binding fragments of the invention contact amino acid residues in both the proximal monomer and in the distal right monomer of the HA trimer. The monomers contacted by the antibodies of the invention, i.e., the proximal monomer and the distal right monomer, may be uncleaved or they may be cleaved to form the HA1 and HA2 polypeptides. In one embodiment, the proximal monomer and the distal right monomer are cleaved. In another embodiment, the proximal monomer and the distal right monomer are uncleaved.

The antibodies and antigen-binding fragments of the invention specifically bind to an epitope that is conserved amongst the 16 different HAs of the 16 subtypes of influenza A virus. In one embodiment, the antibodies or antigen binding fragments of the invention bind to an epitope that comprises the amino acid residue at position 329 of HA1 and the amino acid residues at positions 1, 2, 3, and 4 of HA2, wherein the HA1 and HA2 are present in an uncleaved monomer of the HA trimer.

In another embodiment, the heavy chains of the antibodies or antigen binding fragments of the invention contact the amino acid residue at position 318 in HA1 and amino acid residues at positions 18, 19, 20, 21, 38, 41, 42, 45, 49, 53, and 57 in HA2 of either the proximal or the distal right monomer. The monomers may be uncleaved or cleaved.

In yet another embodiment, the light chains of the antibodies or antigen binding fragments of the invention contact amino acid residues at positions 38, 39, and 43 in HA2 of the uncleaved, proximal monomer, and amino acid residues at positions 327, 328, and 329 in HA1 and 1, 2, 3, and 4 in HA2 of the uncleaved, distal right monomer.

In still another embodiment, the antibodies and antigen-binding fragments of the invention specifically bind to an epitope that comprises the amino acid residue at position 318 of the HA1 and the amino acid residues at positions 18, 19, 20, 21, 38, 39, 41, 42, 43, 45, 48, 49, 53, 56, and 57 of the HA2 of the uncleaved, proximal monomer. In addition, the antibodies specifically bind to an epitope that comprises the amino acid residues at positions 327, 328, 329 of the HA1 and the amino acid residues at positions 1, 2, 3, and 4 of the HA2 polypeptide of the uncleaved, distal right monomer.

In another embodiment, the light chains of the antibodies or antigen binding fragments of the invention contact amino acid residues at positions 38, 39, 42, and 46 in HA2 of the proximal monomer and amino acid residues at positions 321 and 323 in HA1 and 7 and 11 in HA2 of the distal right monomer. In this embodiment both the proximal and distal right monomers are cleaved.

In yet another embodiment, the antibodies and antigen-binding fragments of the invention specifically bind to an epitope that comprises the amino acid residue at position 318 of the HA1 and the amino acid residues at positions 18, 19, 20, 21, 38, 39, 41, 42, 45, 46, 49, 52, 53, and 57 of HA2 of the cleaved proximal monomer, as well as the amino acid residues at positions 321 and 323 of HA1 and amino acid residues at positions 7 and 11 of HA2 of the cleaved distal right monomer.

As shown herein, the antibodies or antigen binding fragments of the invention are capable of binding specifically to the HAs of all 16 subtypes of influenza A virus. In one embodiment, the antibodies of the invention specifically bind to an influenza A HA of subtypes H1, H2, H3, H4, H5, H6, H7, H8, H9, H10, H11, H12, H13, H14, H15 and H16.

In another embodiment of the invention, the invention provides antibodies that have high titers of production. As an example, once two very similar antibodies of the invention, FI6 variant 1 and FI6 variant 2, were isolated, several variants of the antibodies (in particular, variants of FI6 variant 2) were synthesized to improve production in transfected cells. In one embodiment, antibodies or antigen binding fragments of the invention are produced in transfected cells at titers of at least 1.5 fold higher than the titer at which FI6 variant 2 is produced. In another embodiment, the antibodies of the invention are produced at titers of at least 1.8, 2, 2.2, 2.5, 2.7, 3, 3.2, 3.4, 3.6, 3.8, 4, 4.2, 4.4, 4.6, 4.8, 5, 5.3, 5.6 or 6 fold higher than the titer at which FI6 variant 2 is produced. In some embodiments, the antibodies or antigen binding fragments of the invention are produced in transfected cells at titers of at least 3, at least 4, or at least 4.5 fold higher than the titer at which FI6 variant 2 is produced.

Thus, in one embodiment, the invention provides an isolated antibody, or an antigen-binding fragment thereof, that neutralizes infection of a group 1 subtype and a group 2 subtype of influenza A virus and specifically binds to an epitope in the stem region of an influenza A HA trimer, wherein the heavy and light chain of the antibody, or antigen binding fragment thereof, contact amino acids in a first, proximal monomer and a second, distal, right monomer of the HA trimer, and wherein the antibody, or antigen-binding fragment thereof, is produced in transfected cells at titers higher, for example, at least 3 fold higher, than the titer at which FI6 variant 2 is produced.

As described herein, the transfected cells may be any cells now known to, or later discovered by one of skill in the art for expressing the nucleic acid sequences encoding the antibodies of the invention. Examples of such cells include, but are not limited to, mammalian host cells such as CHO, HEK293T, PER.C6, NS0, myeloma or hybridoma cells. Further, the cells may be transfected either transiently or stably. The type of transfection as well as the cell type suitable for use in transfection is within the scope of one of skill in the art.

In another embodiment, the antibody, or antigen binding fragments of the invention, specifically binds to a polypeptide comprising the amino acid sequence of any one of SEQ ID NOs: 37, 38, 39 or 40.

Human monoclonal antibodies, the immortalized B cell clones or the transfected host cells that secrete antibodies of the invention, and nucleic acid encoding the antibodies of the invention are also included within the scope of the invention. As used herein, the term "broad specificity" is used to refer to an antibody or an antigen binding fragment of the invention that can bind and/or neutralize one or more group 1 subtype and one or more group 2 subtype of influenza A virus.

The antibody, or antigen binding fragments, of the invention neutralizes one or more influenza A virus from group 1 (H1, H2, H5, H6, H8, H9, H11, H12, H13, and H16 and their variants) and one or more influenza A virus from group 2 (H3, H4, H7, H10, H14 and H15 and their variants) subtypes. In one embodiment, exemplary group 1 subtypes include H1, H2, H5, H6, and H9 and exemplary group 2 subtypes include H3 and H7.

The antibody and antibody fragment of the invention is capable of neutralizing various combinations of influenza A virus subtypes. In one embodiment, the antibody can neutralize influenza A virus H1 and H3 subtypes, or H2 and H3 subtypes, or H3 and H5 subtypes, or H3 and H9 subtypes, or H1 and H7 subtypes, or H2 and H7 subtypes, or H5 and H7 subtypes, or H7 and H9 subtypes.

In another embodiment, the antibody and antibody fragment of the invention can neutralize influenza A virus H1, H2 and H3 subtypes, or H1, H3 and H5 subtypes, or H1, H3 and H9 subtypes, or H2, H3 and H5 subtypes, or H2, H3 and H9 subtypes, or H3, H5 and H9 subtypes, or H1, H2 and H7 subtypes, or H1, H5 and H7 subtypes, or H1, H7 and H9 subtypes, or H2, H5 and H7 subtypes, or H2, H7 and H9 subtypes, or H5, H7 and H9 subtypes, or H1, H3 and H7 subtypes, or H2, H3 and H7 subtypes, or H3, H5 and H7 subtypes, or H3, H7 and H9 subtypes.

In yet another embodiment, the antibody can neutralize influenza A virus H1, H2, H3 and H7 subtypes, or H1, H3, H5 and H7 subtypes, or H1, H3, H7 and H9 subtypes, or H2, H3, H5 and H7 subtypes, or H2, H3, H7 and H9 subtypes, or H3, H5, H7 and H9 subtypes or H1, H2, H3 and H5 subtypes, or H1, H2, H3 and H9 subtypes, or H1, H3, H5 and H9 subtypes, or H2, H3, H5 and H9 subtypes, or H1, H2, H5 and H7 subtypes, or H1, H2, H7 and H9 subtypes, or H1, H5, H7 and H9 subtypes, or H2, H5, H7 and H9 subtypes.

In still another embodiment, the antibody of the invention can neutralize influenza A virus H1, H2, H3, H5 and H7 subtypes, or H1, H2, H3, H7 and H9 subtypes, or H1, H3, H5, H7 and H9 subtypes, or H2, H3, H5, H7 and H9 subtypes, or H1, H2, H3, H5 and H9 subtypes, or H1, H2, H5, H7 and H9 subtypes, or H1, H2, H3, H5, H7 and H9 subtypes. In yet another embodiment, the antibody and antigen binding fragments of the invention neutralize one or more of the above combinations in addition to neutralizing influenza A virus H6 subtype.

The antibody and antigen binding fragment of the invention have high neutralizing potency. The concentration of the antibody of the invention required for 50% neutralization of influenza A virus, can, for example, be about 50 µg/ml or less. In one embodiment, the concentration of the antibody of the invention required for 50% neutralization of influenza A virus is about 50, 45, 40, 35, 30, 25, 20, 17.5, 15, 12.5, 11, 10, 9, 8, 7, 6, 5, 4.5, 4, 3.5, 3, 2.5, 2, 1.5 or about 1 µg/ml or less. In another embodiment, the concentration of the antibody of the invention required for 50% neutralization of influenza A virus is about 0.9, 0.8, 0.75, 0.7, 0.65, 0.6, 0.55, 0.5, 0.45, 0.4, 0.35, 0.3, 0.25, 0.2, 0.15, 0.1, 0.075, 0.05, 0.04, 0.03, 0.02, 0.01, 0.008, 0.006, 0.004, 0.003, 0.002 or about 0.001 µg/ml or less. This means that only low concentrations of antibody are required for 50% neutralization of influenza A virus. Specificity and potency can be measured using a standard neutralization assay as known to one of skill in the art.

The invention provides an antibody having particularly broad specificity to HA and that neutralizes one or more influenza A virus subtypes from group 1 and one or more influenza A virus subtypes from group 2. The antibody of the invention binds to an epitope in a region of HA that is conserved among two or more influenza A virus subtypes selected from group 1 and group 2.

In one embodiment, the invention provides an antibody, e.g., an isolated antibody or a purified antibody, that specifically binds to a conserved epitope in the stem region of HA of group 1 and group 2 influenza A virus subtypes and interferes with viral replication or spreading. The invention also provides an antibody, e.g., an isolated antibody or a purified antibody, that specifically binds to a conserved epitope in the stem region of HA of group 1 and group 2 subtypes and inhibits virus entry into a cell. Without being bound to any theory, in an exemplary embodiment the antibody or antigen binding fragments of the invention bind to a conserved epitope in the stem region of influenza A virus and inhibit virus entry into a cell by interfering with the fusion step. In one embodiment, the antibody or antigen binding fragments of the invention limit virus spreading by recruiting complement and FcR-expressing killer cells and mediating antibody-dependent cell cytotoxicity (ADCC). An epitope or antigenic determinant of a protein corresponds to those parts of the molecule that are specifically recognized by the binding site (or paratope) of an antibody. Epitopes are thus relational entities that require complementary paratopes for their operational recognition. An epitope that is conserved among different variants of a protein means that the same paratope can specifically recognize these different variants by contacting the same parts of the molecules.

The antibodies of the invention may be monoclonal, for example, human monoclonal antibodies, or recombinant antibodies. The invention also provides fragments of the antibodies of the invention, particularly fragments that retain the antigen-binding activity of the antibodies. Although the specification, including the claims, may, in some places, refer explicitly to antigen binding fragment(s), antibody fragment(s), variant(s) and/or derivative(s) of antibodies, it is understood that the term "antibody" or "antibody of the invention" includes all categories of antibodies, namely, antigen binding fragment(s), antibody fragment(s), variant(s) and derivative(s) of antibodies.

In one embodiment, the antibodies and antibody fragments of the invention neutralize a combination of two or more influenza A virus subtypes of group 1 and group 2. Exemplary influenza A virus subtypes include, but are not limited to, H5N1 (A/Vietnam/1203/04), H1N1 (A/New Caledonia/20/99), H1N1 (A/Salomon Island/3/2006), H3N2 (A/Wyoming/3/03) and H9N2 (A/chicken/Hong Kong/G9/97). In another embodiment, the antibodies neutralize and/or are specific for a combination of 3, 4, 5, 6, 7 or more group 1 and group 2 influenza A virus subtypes.

In an exemplary embodiment, the invention comprises an antibody, or an antibody fragment thereof, that is specific for influenza A virus subtypes H1 and H3 (e.g. H1N1 and H3N2); or H1, H3, H5, and H9 (e.g. H1N1, H3N2, H5N1 and H9N2). In yet another embodiment, the antibody or antibody fragments thereof is specific for H1, H3, H5, H7 and H9 (e.g. H1N1, H3N2, H5N1, H7N1, H7N7, H9N2). Other exemplary combinations of subtypes of influenza A virus are provided earlier in the application.

The SEQ ID numbers for the amino acid sequence for the heavy chain variable region (VH) and the light chain variable region (VL) of exemplary antibodies of the invention as well as the SEQ ID numbers for the nucleic acid sequences encoding them are listed in Table 1.

TABLE 1

SEQ ID Numbers for $V_H$ and $V_L$ Polypeptides and Polynucleotides for Exemplary Influenza A Virus Neutralizing Antibodies

| | SEQ ID NOs. for $V_H$ and $V_L$ Polypeptides and Polynucleotides | | | |
|---|---|---|---|---|
| | $V_H$ Polypeptide | $V_L$ Polypeptide | $V_H$ Polynucleotide | $V_L$ Polynucleotide |
| FI6 variant 1 | 13 | 14 | 15 | 16 |
| FI6 variant 2 | 33 | 14 | 34 | 16 |

TABLE 1-continued

SEQ ID Numbers for $V_H$ and $V_L$ Polypeptides and Polynucleotides for Exemplary Influenza A Virus Neutralizing Antibodies

| | SEQ ID NOs. for $V_H$ and $V_L$ Polypeptides and Polynucleotides | | | |
|---|---|---|---|---|
| | $V_H$ Polypeptide | $V_L$ Polypeptide | $V_H$ Polynucleotide | $V_L$ Polynucleotide |
| FI6 variant 3 | 55 | 57 | 56 | 58 |
| FI6 variant 4 | 59 | 57 | 60 | 58 |
| FI6 variant 5 | 59 | 61 | 60 | 62 |
| FI28 variant 1 | 29 | 30 | 31 | 32 |
| FI28 variant 2 | 35 | 30 | 36 | 32 |

In one embodiment, an antibody or antibody fragment of the invention comprises a heavy chain variable region having an amino acid sequence that is about 70%, 75%, 80%, 85%, 90%, 95%, 97%, 98%, 99% or 100% identical to the sequence recited in any one of SEQ ID NOs: 13, 33, 55, 59, 29 or 35. In another embodiment, an antibody or antibody fragment of the invention comprises a light chain variable region having an amino acid sequence that is about 70%, 75%, 80%, 85%, 90%, 95%, 97%, 98%, 99% or 100% identical to the sequence recited in SEQ ID NOs: 14, 57, 61 or 30.

In yet another embodiment, the heavy chain variable region of an antibody of the invention may be encoded by a nucleic acid that has a sequence that is about 70%, 75%, 80%, 85%, 90%, 95%, 97%, 98%, 99% or 100% identical to the sequence recited in any one of SEQ ID NOs: 15, 34, 56, 60, 31 or 36. In yet another embodiment, the light chain variable region of an antibody of the invention may be encoded by a nucleic acid that has a sequence that is about 70%, 75%, 80%, 85%, 90%, 95%, 97%, 98%, 99% or 100% identical to the sequence recited in SEQ ID NOs: 16, 58, 62, or 32.

The CDRs of the antibody heavy chains are referred to as CDRH1 (or HCDR1), CDRH2 (or HCDR2) and CDRH3 (or HCDR3), respectively. Similarly, the CDRs of the antibody light chains are referred to as CDRL1 (or LCDR1), CDRL2 (or LCDR1) and CDRL3 (or LCDR1), respectively. The positions of the CDR amino acids are defined according to the IMGT numbering system as: CDR1-IMGT positions 27 to 38, CDR2-IMGT positions 56 to 65 and CDR3-IMGT positions 105 to 117.

Table 2 provides the SEQ ID numbers for the amino acid sequences of the six CDRs of the heavy and light chains, respectively, of the exemplary antibodies of the invention.

TABLE 2

SEQ ID Numbers for CDR Polypeptides of Exemplary Influenza A Virus Neutralizing Antibodies

| | SEQ ID NOs. for CDR Polypeptides | | | | | |
|---|---|---|---|---|---|---|
| | CDRH1 | CDRH2 | CDRH3 | CDRL1 | CDRL2 | CDRL3 |
| FI6 variant 1 | 1 | 2 | 3 | 4 | 5 | 6 |
| FI6 variant 2 | 1 | 2 | 3 | 4 | 5 | 6 |
| FI6 variant 3 | 1 | 41 | 42 | 4 | 5 | 6 |
| FI6 variant 4 | 1 | 41 | 43 | 4 | 5 | 6 |
| FI6 variant 5 | 1 | 41 | 43 | 44 | 5 | 6 |
| FI28 variant 1 | 17 | 18 | 19 | 20 | 21 | 22 |
| FI28 variant 2 | 17 | 18 | 19 | 20 | 21 | 22 |

In one embodiment, an antibody or antibody fragment of the invention comprises at least one CDR with a sequence that has at least 95% sequence identity to any one of SEQ ID NOs: 1-6, 41-44 or 17-22, In another embodiment, the invention provides an antibody comprising a heavy chain comprising one or more (i.e. one, two or all three) heavy chain CDRs from FI6 variant 1, FI6 variant 2, FI6 variant 3, FI6 variant 4, FI6 variant 5, FI28 variant 1 or FI28 variant 2. In an exemplary embodiment, the antibody or antigen binding fragment of the invention comprises a heavy chain CDR1 with the amino acid sequence of SEQ ID NO: 1 or SEQ ID NO: 17; a heavy chain CDR2 with the amino acid sequence of SEQ ID NO: 2, SEQ ID NO: 41 or SEQ ID NO: 18; and a heavy chain CDR3 with the amino acid sequence of SEQ ID NO: 3, SEQ ID NO: 42, SEQ ID NO: 43 or SEQ ID NO: 19. In certain embodiments, an antibody or antibody fragment as provided herein comprises a heavy chain comprising (i) SEQ ID NO: 1 for CDRH1, SEQ ID NO: 2 for CDRH2 and SEQ ID NO: 3 for CDRH3, (ii) SEQ ID NO: 1 for CDRH1, SEQ ID NO: 41 for CDRH2 and SEQ ID NO: 42 for CDRH3, (iii) SEQ ID NO: 1 for CDRH1, SEQ ID NO: 41 for CDRH2 and SEQ ID NO: 43 for CDRH3, or (iv) SEQ ID NO: 17 for CDRH1, SEQ ID NO: 18 for CDRH2 and SEQ ID NO: 19 for CDRH3.

Also provided is an antibody comprising a light chain comprising one or more (i.e. one, two or all three) light chain CDRs from FI6 variant 1, FI6 variant 2, FI6 variant 3, FI6 variant 4, FI6 variant 5, FI28 variant 1 or FI28 variant 2. In an exemplary embodiment, the antibody or antigen binding fragment of the invention comprises a light chain CDR1 with the amino acid sequence of SEQ ID NO: 4, SEQ ID NO: 44 or SEQ ID NO: 20; a light chain CDR2 with the amino acid sequence of SEQ ID NO: 5 or SEQ ID NO: 21; and a light chain CDR3 with the amino acid sequence of SEQ ID NO: 6 or SEQ ID NO: 22. In certain embodiments, an antibody as provided herein comprises a light chain comprising (i) SEQ ID NO: 4 for CDRL1, SEQ ID NO: 5 for CDRL2 and SEQ ID NO: 6 for CDRL3, (ii) SEQ ID NO: 44 for CDRL1, SEQ ID NO: 5 for CDRL2 and SEQ ID NO: 6 for CDRL3 or (iii) SEQ ID NO: 20 for CDRL1, SEQ ID NO: 21 for CDRL2 and SEQ ID NO: 22 for CDRL3.

In one embodiment, an antibody of the invention, or antigen binding fragment thereof, comprises all of the CDRs of antibody FI6 variant 1 as listed in Table 2, and neutralizes influenza A virus infection. In another embodiment, an antibody of the invention, or antigen binding fragment thereof, comprises all of the CDRs of antibody FI6 variant 2 as listed in Table 2, and neutralizes influenza A virus infection. In another embodiment, an antibody of the invention, or antigen binding fragment thereof, comprises all of the CDRs of antibody FI6 variant 3 as listed in Table 2, and neutralizes influenza A virus infection. In another embodiment, an antibody of the invention, or antigen binding fragment thereof, comprises all of the CDRs of antibody FI6 variant 4 as listed in Table 2, and neutralizes influenza A virus infection. In another embodiment, an antibody of the invention, or antigen binding fragment thereof, comprises all of the CDRs of antibody FI6 variant 5 as listed in Table 2, and neutralizes influenza A virus infection.

In yet another embodiment, an antibody of the invention, or antigen binding fragment thereof, comprises all of the CDRs of antibody FI28 variant 1 as listed in Table 2, and neutralizes influenza A virus infection. In still another embodiment, an antibody of the invention, or antigen binding fragment thereof, comprises all of the CDRs of antibody FI28 variant 2 as listed in Table 2, and neutralizes influenza A virus infection.

Examples of antibodies of the invention include, but are not limited to, FI6 variant 1, FI6 variant 2, FI6 variant 3, FI6 variant 4, FI6 variant 5, FI28 variant 1 and FI28 variant 2.

The invention further comprises an antibody, or fragment thereof, that binds to the same epitope as an antibody of the invention, or an antibody that competes with an antibody or antigen binding fragment of the invention.

Antibodies of the invention also include hybrid antibody molecules that comprise one or more CDRs from an antibody of the invention and one or more CDRs from another antibody to the same epitope. In one embodiment, such hybrid antibodies comprise three CDRs from an antibody of the invention and three CDRs from another antibody to the same epitope. Exemplary hybrid antibodies comprise i) the three light chain CDRs from an antibody of the invention and the three heavy chain CDRs from another antibody to the same epitope, or ii) the three heavy chain CDRs from an antibody of the invention and the three light chain CDRs from another antibody to the same epitope.

Variant antibodies are also included within the scope of the invention. Thus, variants of the sequences recited in the application are also included within the scope of the invention. Such variants include natural variants generated by somatic mutation in vivo during the immune response or in vitro upon culture of immortalized B cell clones. Alternatively, variants may arise due to the degeneracy of the genetic code, as mentioned above or may be produced due to errors in transcription or translation.

Further variants of the antibody sequences having improved affinity and/or potency may be obtained using methods known in the art and are included within the scope of the invention. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences of the invention are also within the scope of the invention.

In one embodiment variant antibody sequences may share 70% or more (i.e. 75%, 80%, 85%, 90%, 95%, 97%, 98%, 99% or more) amino acid sequence identity with the sequences recited in the application. In some embodiments such sequence identity is calculated with regard to the full length of the reference sequence (i.e. the sequence recited in the application). In some further embodiments, percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

In another aspect, the invention also includes nucleic acid sequences encoding part or all of the light and heavy chains and CDRs of the antibodies of the present invention. Provided herein are nucleic acid sequences encoding part or all of the light and heavy chains and CDRs of exemplary antibodies of the invention. Table 1 provides the SEQ ID numbers for the nucleic acid sequences encoding the heavy chain and light chain variable regions of the exemplary antibodies of the invention. For example, nucleic acid sequences provided herein include SEQ ID NO: 15 (encoding the FI6 variant 1 heavy chain variable region), SEQ ID NO: 16 (encoding the FI6 variant 1 and FI6 variant 2 light chain variable region), SEQ ID NO: 34 (encoding the FI6 variant 2 heavy chain variable region), SEQ ID NO: 56 (encoding the FI6 variant 3 heavy chain variable region), SEQ ID NO: 58 (encoding the FI6 variant 3 and FI6 variant 4 light chain variable region), SEQ ID NO: 60 (encoding the FI6 variant 4 and FI6 variant 5 heavy chain variable region), SEQ ID NO: 62 (encoding the FI6 variant 5 light chain variable region), SEQ ID NO: 31 (encoding the FI28 variant 1 heavy chain variable region), SEQ ID NO: 36 (encoding the FI28 variant 2 heavy chain variable region) and SEQ ID NO: 32 (encoding the FI28 variant 1 and variant 2 light chain variable region).

Table 3 provides the SEQ ID numbers for the nucleic acid sequences encoding the CDRs of the exemplary antibodies of the invention. Due to the redundancy of the genetic code, variants of these sequences will exist that encode the same amino acid sequences.

TABLE 3

SEQ ID Numbers for CDR Polynucleotides of Exemplary Influenza A Virus Neutralizing Antibodies:

| | SEQ ID NOs. for CDR Polynucleotides | | | | | |
|---|---|---|---|---|---|---|
| | CDRH1 | CDRH2 | CDRH3 | CDRL1 | CDRL2 | CDRL3 |
| FI6 variant 1 | 7 | 8 | 9 | 10 | 11 | 12 |
| FI6 variant 2 | 7 | 8 | 9 | 10 | 11 | 12 |
| FI6 variant 3 | 45 | 46 | 47 | 48 | 49 | 50 |
| FI6 variant 4 | 51 | 52 | 53 | 48 | 49 | 50 |
| FI6 variant 5 | 51 | 52 | 53 | 54 | 49 | 50 |
| FI28 variant 1 | 23 | 24 | 25 | 26 | 27 | 28 |
| FI28 variant 2 | 23 | 24 | 25 | 26 | 27 | 28 |

In one embodiment, nucleic acid sequences according to the invention include nucleic acid sequences having at least 70%, at least 75%, at least 80%, at least 85%, at least 90%, at least 95%, at least 98%, or at least 99% identity to the nucleic acid encoding a heavy or light chain of an antibody of the invention. In another embodiment, a nucleic acid sequence of the invention has the sequence of a nucleic acid encoding a heavy or light chain CDR of an antibody of the invention. For example, a nucleic acid sequence according to the invention comprises a sequence that is at least 75% identical to the nucleic acid sequences of SEQ ID NOs: 7-12, 15, 16, 34, 23-28, 31, 32, 36, 45-54, 56, 58, 60 or 62.

Further included within the scope of the invention are vectors, for example, expression vectors, comprising a nucleic acid sequence according to the invention. Cells transformed with such vectors are also included within the scope of the invention. Examples of such cells include but are not limited to, eukaryotic cells, e.g. yeast cells, animal cells or plant cells. In one embodiment the cells are mammalian, e.g. human, CHO, HEK293T, PER.C6, NS0, myeloma or hybridoma cells.

The invention also relates to monoclonal antibodies that bind to an epitope capable of binding the antibodies of the invention, including, but not limited to, a monoclonal antibody selected from the group consisting FI6 variant 1, FI6 variant 2, FI6 variant 3, FI6 variant 4, FI6 variant 5, FI28 variant 1 and FI28 variant 2.

Monoclonal and recombinant antibodies are particularly useful in identification and purification of the individual polypeptides or other antigens against which they are directed. The antibodies of the invention have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme. The antibodies may also be used for the molecular identification and characterization (epitope mapping) of antigens.

Antibodies of the invention can be coupled to a drug for delivery to a treatment site or coupled to a detectable label to facilitate imaging of a site comprising cells of interest, such as cells infected with influenza A virus. Methods for coupling antibodies to drugs and detectable labels are well known in the art, as are methods for imaging using detectable labels. Labelled antibodies may be employed in a wide variety of assays, employing a wide variety of labels. Detection of the formation of an antibody-antigen complex between an antibody of the invention and an epitope of interest (an influenza A virus epitope) can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include 125I, 131I, 35S, or 3H. Such labelled reagents may be used in a variety of well-known assays, such as radioimmunoassays, enzyme immunoassays, e.g., ELISA, fluorescent immunoassays, and the like. (See U.S. Pat. No. 3,766,162; U.S. Pat. No. 3,791,932; U.S. Pat. No. 3,817,837; and U.S. Pat. No. 4,233,402 for example).

An antibody according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurds, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158.

Alternatively, an antibody, or antibody fragment thereof, can be conjugated to a second antibody, or antibody fragment thereof, to form an antibody heteroconjugate as described in U.S. Pat. No. 4,676,980. In addition, linkers may be used between the labels and the antibodies of the invention (e.g.

U.S. Pat. No. 4,831,175). Antibodies or, antigen-binding fragments thereof may be directly labelled with radioactive iodine, indium, yttrium, or other radioactive particle known in the art (e.g. U.S. Pat. No. 5,595,721). Treatment may consist of a combination of treatment with conjugated and non-conjugated antibodies administered simultaneously or subsequently (e.g. WO00/52031; WO00/52473).

Antibodies of the invention may also be attached to a solid support. Additionally, antibodies of the invention, or functional antibody fragments thereof, can be chemically modified by covalent conjugation to a polymer to, for example, increase their circulating half-life. Examples of polymers, and methods to attach them to peptides, are shown in U.S. Pat. No. 4,766,106; U.S. Pat. No. 4,179,337; U.S. Pat. No. 4,495,285 and U.S. Pat. No. 4,609,546. In some embodiments the polymers may be selected from polyoxyethylated polyols and polyethylene glycol (PEG). PEG is soluble in water at room temperature and has the general formula: $R(O-CH_2-CH_2)_n O-R$ where R can be hydrogen, or a protective group such as an alkyl or alkanol group. In one embodiment the protective group may have between 1 and 8 carbons. In a further embodiment the protective group is methyl. The symbol n is a positive integer. In one embodiment n is between 1 and 1,000. In another embodiment n is between 2 and 500. In one embodiment the PEG has an average molecular weight between 1,000 and 40,000. In a further embodiment the PEG has a molecular weight between 2,000 and 20,000. In yet a further embodiment the PEG has a molecular weight between 3,000 and 12,000. In one embodiment PEG has at least one hydroxy group. In another embodiment the PEG has a terminal hydroxy group. In yet another embodiment it is the terminal hydroxy group which is activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. In one embodiment, POG is used. Without being bound by any theory, because the glycerol backbone of polyoxyethylated glycerol is the same backbone occurring naturally in, for example, animals and humans in mono-, di-, triglycerides, this branching would not necessarily be seen as a foreign agent in the body. In some embodiments POG has a molecular weight in the same range as PEG. Another drug delivery system that can be used for increasing circulatory half-life is the liposome. Methods of preparing liposome delivery systems are discussed in Gabizon et al. (1982), Cafiso (1981) and Szoka (1980). Other drug delivery systems are known in the art and are described in, for example, referenced in Poznansky et al. (1980) and Poznansky (1984).

Antibodies of the invention may be provided in purified form. Typically, the antibody will be present in a composition that is substantially free of other polypeptides e.g. where less than 90% (by weight), usually less than 60% and more usually less than 50% of the composition is made up of other polypeptides.

Antibodies of the invention may be immunogenic in non-human (or heterologous) hosts e.g. in mice. In particular, the antibodies may have an idiotope that is immunogenic in non-human hosts, but not in a human host. Antibodies of the invention for human use include those that cannot be easily isolated from hosts such as mice, goats, rabbits, rats, non-primate mammals, etc. and cannot generally be obtained by humanisation or from xeno-mice.

Antibodies of the invention can be of any isotype (e.g. IgA, IgG, IgM i.e. an α, γ or μ heavy chain), but will generally be IgG. Within the IgG isotype, antibodies may be IgG1, IgG2, IgG3 or IgG4 subclass. Antibodies of the invention may have a κ or a λ light chain.

Production of Antibodies

Antibodies according to the invention can be made by any method known in the art. For example, the general methodology for making monoclonal antibodies using hybridoma technology is well known (Kohler, G. and Milstein, C, 1975; Kozbar et al. 1983). In one embodiment, the alternative EBV immortalisation method described in WO2004/076677 is used.

Using the method described in WO2004/076677, B cells producing the antibody of the invention can be transformed with EBV in the presence of a polyclonal B cell activator. Transformation with EBV is a standard technique and can easily be adapted to include polyclonal B cell activators.

Additional stimulants of cellular growth and differentiation may optionally be added during the transformation step to further enhance the efficiency. These stimulants may be cytokines such as IL-2 and IL-15. In one aspect, IL-2 is added during the immortalisation step to further improve the efficiency of immortalisation, but its use is not essential. The immortalized B cells produced using these methods can then be cultured using methods known in the art and antibodies isolated therefrom.

Using the method described in UK Patent Application 0819376.5, single plasma cells can be cultured in microwell culture plates. Antibodies can be isolated from the single plasma cell cultures. Further, from single plasma cell cultures, RNA can be extracted and single cell PCR can be performed using methods known in the art. The VH and VL regions of the antibodies can be amplified by RT-PCR, sequenced and cloned into an expression vector that is then transfected into HEK293T cells or other host cells. The cloning of nucleic acid in expression vectors, the transfection of host cells, the culture of the transfected host cells and the isolation of the produced antibody can be done using any methods known to one of skill in the art.

The antibodies may be further purified, if desired, using filtration, centrifugation and various chromatographic methods such as HPLC or affinity chromatography. Techniques for purification of antibodies, e.g., monoclonal antibodies, including techniques for producing pharmaceutical-grade antibodies, are well known in the art.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" may include Fab, Fab', F(ab')2 and Fv fragments. The invention also encompasses single-chain Fv fragments (scFv) derived from the heavy and light chains of an antibody of the invention e.g. the invention includes a scFv comprising the CDRs from an antibody of the invention. Also included are heavy or light chain monomers and dimers, single domain heavy chain antibodies, single domain light chain antibodies, as well as single chain antibodies, e.g. single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fab3, bispecific scFv, and diabodies (Holliger and Hudson, 2005, Nature Biotechnology 9: 1126-1136).

Standard techniques of molecular biology may be used to prepare DNA sequences encoding the antibodies or antibody fragments of the present invention. Desired DNA sequences may be synthesised completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example E. coli, and other microbial systems may be used, in part, for expression of antibody fragments such as Fab and F(ab')2 fragments, and especially Fv fragments and single chain antibody fragments, for example, single chain Fvs. Eukaryotic, e.g. mammalian, host cell expression systems may be used for production of larger antibody molecules, including complete antibody molecules. Suitable mammalian host cells include, but are not limited to, CHO, HEK293T, PER.C6, NS0, myeloma or hybridoma cells.

The present invention also provides a process for the production of an antibody molecule according to the present invention comprising culturing a host cell comprising a vector encoding a nucleic acid of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Alternatively, antibodies according to the invention may be produced by i) expressing a nucleic acid sequence according to the invention in a host cell, and ii) isolating the expressed antibody product. Additionally, the method may include iii) purifying the antibody.

Screening of Transformed B Cells, Cultured Single Plasma Cells and Transfected HEK293T Cells Transformed B cells and cultured single plasma cells may be screened for those producing antibodies of the desired specificity or function.

The screening step may be carried out by any immunoassay, for example, ELISA, by staining of tissues or cells (including transfected cells), by neutralization assay or by one of a number of other methods known in the art for identifying desired specificity or function. The assay may select on the basis of simple recognition of one or more antigens, or may select on the additional basis of a desired function e.g. to select neutralizing antibodies rather than just antigen-binding antibodies, to select antibodies that can change characteristics of targeted cells, such as their signalling cascades, their shape, their growth rate, their capability of influencing other cells, their response to the influence by other cells or by other reagents or by a change in conditions, their differentiation status, etc.

Individual transformed B cell clones may then be produced from the positive transformed B cell culture. The cloning step for separating individual clones from the mixture of positive cells may be carried out using limiting dilution, micromanipulation, single cell deposition by cell sorting or another method known in the art.

Nucleic acid from the cultured single plasma cells can be isolated, cloned and expressed in HEK293T cells or other host cells using methods known in the art.

The immortalized B cell clones or the transfected HEK293T cells of the invention can be used in various ways e.g. as a source of monoclonal antibodies, as a source of nucleic acid (DNA or mRNA) encoding a monoclonal antibody of interest, for research, etc.

The invention provides a composition comprising immortalized B memory cells or transfected host cells that produce antibodies that neutralize at least two different subtypes of influenza A virus selected from group 1 and group 2 subtypes.

Epitopes

As mentioned above, the antibodies of the invention can be used to map the epitopes to which they bind. The inventors have discovered that the antibodies neutralizing influenza A virus infection are directed towards epitopes found on HA. In one embodiment, the antibodies are directed to one or more epitopes in the stem region of HA that are conserved among one or more group 1 and group 2 subtypes of influenza A virus. The epitopes to which the antibodies of the invention bind may be linear (continuous) or conformational (discontinuous). In one embodiment, the antibodies and antibody fragments of the invention bind a region of the polypeptide comprising SEQ ID NOs: 37, 38, 39 or 40, as discussed herein.

In another embodiment, the epitope to which the antibodies of the invention bind comprises amino acid residues in the HA1 and HA2 polypeptides of one or two HA monomers as described above. The HA monomers can be uncleaved or cleaved.

The epitopes recognized by the antibodies of the present invention may have a number of uses. The epitope and mimotopes thereof in purified or synthetic form can be used to raise immune responses (i.e., as a vaccine, or for the production of antibodies for other uses) or for screening sera for antibodies that immunoreact with the epitope or mimotopes thereof. In one embodiment such an epitope or mimotope, or antigen comprising such an epitope or mimotope may be used as a vaccine for raising an immune response. The antibodies and antibody fragments of the invention can also be used in a method of monitoring the quality of vaccines. In particular the antibodies can be used to check that the antigen in a vaccine contains the correct immunogenic epitope in the correct conformation.

The epitope may also be useful in screening for ligands that bind to said epitope. Such ligands, include but are not limited to antibodies; including those from camels, sharks and other species, fragments of antibodies, peptides, phage display technology products, aptamers, adnectins or fragments of other viral or cellular proteins, may block the epitope and so prevent infection. Such ligands are encompassed within the scope of the invention.

Recombinant Expression

The immortalized B cell clone or the cultured plasma cell of the invention may also be used as a source of nucleic acid for the cloning of antibody genes for subsequent recombinant expression. Expression from recombinant sources is more common for pharmaceutical purposes than expression from B cells or hybridomas e.g. for reasons of stability, reproducibility, culture ease, etc.

Thus the invention provides a method for preparing a recombinant cell, comprising the steps of: (i) obtaining one or more nucleic acids (e.g. heavy and/or light chain mRNAs) from the B cell clone or the cultured single plasma cell that encodes the antibody of interest; (ii) inserting the nucleic acid into an expression vector and (iii) transfecting the vector into a host cell in order to permit expression of the antibody of interest in that host cell.

Similarly, the invention provides a method for preparing a recombinant cell, comprising the steps of: (i) sequencing nucleic acid(s) from the B cell clone or the cultured single plasma cell that encodes the antibody of interest; and (ii) using the sequence information from step (i) to prepare nucleic acid(s) for insertion into a host cell in order to permit expression of the antibody of interest in that host cell. The nucleic acid may, but need not, be manipulated between steps (i) and (ii) to introduce restriction sites, to change codon usage, and/or to optimise transcription and/or translation regulatory sequences.

The invention also provides a method of preparing a transfected host cell, comprising the step of transfecting a host cell with one or more nucleic acids that encode an antibody of interest, wherein the nucleic acids are nucleic acids that were derived from an immortalized B cell clone or a cultured single plasma cell of the invention. Thus the procedures for first preparing the nucleic acid(s) and then using it to transfect a host cell can be performed at different times by different people in different places (e.g. in different countries).

These recombinant cells of the invention can then be used for expression and culture purposes. They are particularly useful for expression of antibodies for large-scale pharmaceutical production. They can also be used as the active ingredient of a pharmaceutical composition. Any suitable culture technique can be used, including but not limited to static culture, roller bottle culture, ascites fluid, hollow-fiber type bioreactor cartridge, modular minifermenter, stirred tank, microcarrier culture, ceramic core perfusion, etc.

Methods for obtaining and sequencing immunoglobulin genes from B cells or plasma cells are well known in the art (e.g. see Chapter 4 of Kuby Immunology, 4th edition, 2000).

The transfected host cell may be a eukaryotic cell, including yeast and animal cells, particularly mammalian cells (e.g. CHO cells, NS0 cells, human cells such as PER.C6 (Jones et al 2003) or HKB-11 (Cho et al. 2001; Cho et al. 2003) cells, myeloma cells (U.S. Pat. No. 5,807,715; U.S. Pat. No. 6,300,104 etc.)), as well as plant cells. Preferred expression hosts can glycosylate the antibody of the invention, particularly with carbohydrate structures that are not themselves immunogenic in humans. In one embodiment the transfected host cell may be able to grow in serum-free media. In a further embodiment the transfected host cell may be able to grow in culture without the presence of animal-derived products. The transfected host cell may also be cultured to give a cell line.

The invention provides a method for preparing one or more nucleic acid molecules (e.g. heavy and light chain genes) that encode an antibody of interest, comprising the steps of: (i) preparing an immortalized B cell clone or culturing a plasma cell according to the invention; (ii) obtaining from the B cell clone or the cultured single plasma cell nucleic acid that encodes the antibody of interest. The invention also provides a method for obtaining a nucleic acid sequence that encodes an antibody of interest, comprising the steps of: (i) preparing an immortalized B cell clone or culturing a single plasma cell according to the invention; (ii) sequencing nucleic acid from the B cell clone or the cultured plasma cell that encodes the antibody of interest.

The invention also provides a method of preparing nucleic acid molecule(s) that encodes an antibody of interest, comprising the step of obtaining the nucleic acid that was obtained from a transformed B cell clone or a cultured plasma cell of the invention. Thus the procedures for first obtaining the B cell clone or the cultured plasma cell, and then obtaining nucleic acid(s) from the B cell clone or the cultured plasma cell can be performed at different times by different people in different places (e.g. in different countries).

The invention provides a method for preparing an antibody (e.g. for pharmaceutical use), comprising the steps of: (i) obtaining and/or sequencing one or more nucleic acids (e.g. heavy and light chain genes) from the selected B cell clone or the cultured plasma cell expressing the antibody of interest; (ii) inserting the nucleic acid(s) into or using the nucleic acid(s) sequence(s) to prepare an expression vector; (iii) transfect a host cell that can express the antibody of interest; (iv) culturing or sub-culturing the transfected host cells under conditions where the antibody of interest is expressed; and, optionally, (v) purifying the antibody of interest.

The invention also provides a method of preparing an antibody comprising the steps of: culturing or sub-culturing a transfected host cell population under conditions where the antibody of interest is expressed and, optionally, purifying the antibody of interest, wherein said transfected host cell population has been prepared by (i) providing nucleic acid(s) encoding a selected antibody of interest that is produced by a B cell clone or a cultured plasma cell prepared as described above, (ii) inserting the nucleic acid(s) into an expression vector, (iii) transfecting the vector in a host cell that can express the antibody of interest, and (iv) culturing or sub-culturing the transfected host cell comprising the inserted nucleic acids to produce the antibody of interest. Thus the procedures for first preparing the recombinant host cell and then culturing it to express antibody can be performed at very different times by different people in different places (e.g., in different countries).

Pharmaceutical Compositions

The invention provides a pharmaceutical composition containing the antibodies and/or antibody fragments of the invention and/or nucleic acid encoding such antibodies and/or the epitopes recognised by the antibodies of the invention. A pharmaceutical composition may also contain a pharmaceutically acceptable carrier to allow administration. The carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the subject.

Within the scope of the invention, forms of administration may include those forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. In one embodiment the compositions are adapted for administration to human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule. Known antibody-based pharmaceuticals provide guidance relating to frequency of administration e.g. whether a pharmaceutical should be delivered daily, weekly, monthly, etc. Frequency and dosage may also depend on the severity of symptoms.

Compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition, like Synagis™ and Herceptin™, for reconstitution with sterile water containing a preservative). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a subject. For example, a lyophilised antibody can be provided in kit form with sterile water or a sterile buffer.

It will be appreciated that the active ingredient in the composition will be an antibody molecule, an antibody fragment or variants and derivatives thereof. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Gennaro (2000) Remington: The Science and Practice of Pharmacy, 20th edition, ISBN: 0683306472.

Pharmaceutical compositions of the invention generally have a pH between 5.5 and 8.5, in some embodiments this may be between 6 and 8, and in further embodiments about 7. The pH may be maintained by the use of a buffer. The composition may be sterile and/or pyrogen free. The composition may be isotonic with respect to humans. In one embodiment pharmaceutical compositions of the invention are supplied in hermetically-sealed containers.

Pharmaceutical compositions will include an effective amount of one or more antibodies of the invention and/or a polypeptide comprising an epitope that binds an antibody of the invention i.e. an amount that is sufficient to treat, ameliorate, or prevent a desired disease or condition, or to exhibit a detectable therapeutic effect. Therapeutic effects also include reduction in physical symptoms. The precise effective amount for any particular subject will depend upon their size and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.01 mg/kg to about 50 mg/kg, or about 0.05 mg/kg to about 10 mg/kg of the compositions of the present invention in the individual to which it is administered. Known antibody-based pharmaceuticals provide guidance in this respect e.g. Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m2; etc.

In one embodiment compositions can include more than one (e.g. 2, 3, etc.) antibodies of the invention to provide an additive or synergistic therapeutic effect. In another embodiment, the composition may comprise one or more (e.g. 2, 3, etc.) antibodies of the invention and one or more (e.g. 2, 3, etc.) additional antibodies against influenza A or influenza B virus. For example, one antibody may bind to a HA epitope, while another may bind to a different epitope on HA, or to an epitope on the neuraminidase and/or matrix proteins. Further, the administration of antibodies of the invention together with an influenza A vaccine or with antibodies of specificities other than influenza A virus, for example, influenza B virus, are within the scope of the invention. The antibodies of the invention can be administered either combined/simultaneously or at separate times from an influenza vaccine or from antibodies of specificities other than influenza A virus.

In another embodiment, the invention provides a pharmaceutical composition comprising two or more antibodies, wherein the first antibody is an antibody of the invention and is specific for an HA epitope, and the second antibody is specific for a neuraminidase epitope, a second HA epitope and/or a matrix epitope. For example, the invention provides a pharmaceutical composition comprising two or more antibodies, wherein the first antibody is specific for an epitope in the stem of an influenza A virus HA, and the second antibody is specific for a neuraminidase epitope, a second HA epitope (for example, an epitope in the globular head of HA, a second epitope in the stem of HA), and/or a matrix epitope. The second epitope in the stem or the epitope in the globular head of the influenza A virus HA may, but need not, be conserved among more than one influenza A virus subtype.

In yet another embodiment, the invention provides a pharmaceutical composition comprising two or more antibodies, wherein the first antibody is specific for a neuraminidase epitope, and the second antibody is specific for a second neuraminidase epitope, a HA epitope and/or a matrix epitope.

In still another embodiment, the invention provides a pharmaceutical composition comprising two or more antibodies, wherein the first antibody is specific for a matrix epitope, and the second antibody is specific for a second matrix epitope, an epitope on HA and/or neuraminidase.

Exemplary antibodies of the invention specific for an Influenza A virus target protein include, but are not limited to, FI6 variant 1, FI6 variant 2, FI6 variant 3, FI6 variant 4, FI6 variant 5, FI28 variant 1 or FI28 variant 2.

In one embodiment, the invention provides a pharmaceutical composition comprising the antibody FI6 variant 1 or an antigen binding fragment thereof, and a pharmaceutically acceptable carrier. In another embodiment, the invention provides a pharmaceutical composition comprising the antibody FI6 variant 2 or an antigen binding fragment thereof, and a pharmaceutically acceptable carrier. In another embodiment, the invention provides a pharmaceutical composition comprising the antibody FI6 variant 3 or an antigen binding fragment thereof, and a pharmaceutically acceptable carrier. In another embodiment, the invention provides a pharmaceutical composition comprising the antibody FI6 variant 4 or an antigen binding fragment thereof, and a pharmaceutically acceptable carrier. In another embodiment, the invention provides a pharmaceutical composition comprising the antibody FI6 variant 5 or an antigen binding fragment thereof, and a pharmaceutically acceptable carrier. In yet another embodiment, the invention provides a pharmaceutical composition comprising the antibody FI28 variant 1 or an antigen binding fragment thereof, and a pharmaceutically acceptable carrier. In still another embodiment, the invention provides a pharmaceutical composition comprising the antibody FI28 variant 2 or an antigen binding fragment thereof, and a pharmaceutically acceptable carrier.

Antibodies of the invention may be administered (either combined or separately) with other therapeutics e.g. with chemotherapeutic compounds, with radiotherapy, etc. In one embodiment, the therapeutic compounds include anti-viral compounds such as Tamiflu™. Such combination therapy provides an additive or synergistic improvement in therapeutic efficacy relative to the individual therapeutic agents when administered alone. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

Antibodies may be administered to those subjects who have previously shown no response to treatment for influenza A virus infection, i.e. have been shown to be refractive to anti-influenza treatment. Such treatment may include previous treatment with an anti-viral agent. This may be due to, for example, infection with an anti-viral resistant strain of influenza A virus.

In one embodiment, a composition of the invention may include antibodies of the invention, wherein the antibodies may make up at least 50% by weight (e.g. 60%, 70%, 75%, 80%, 85%, 90%, 95%, 97%, 98%, 99% or more) of the total protein in the composition. In such a composition, the antibodies are in purified form.

The invention provides a method of preparing a pharmaceutical, comprising the steps of: (i) preparing an antibody of the invention; and (ii) admixing the purified antibody with one or more pharmaceutically-acceptable carriers.

The invention also provides a method of preparing a pharmaceutical, comprising the step of admixing an antibody with one or more pharmaceutically-acceptable carriers, wherein the antibody is a monoclonal antibody that was obtained from a transformed B cell or a cultured plasma cell of the invention. Thus the procedures for first obtaining the monoclonal antibody and then preparing the pharmaceutical can be performed at very different times by different people in different places (e.g. in different countries).

As an alternative to delivering antibodies or B cells for therapeutic purposes, it is possible to deliver nucleic acid (typically DNA) that encodes the monoclonal antibody (or active fragment thereof) of interest derived from the B cell or the cultured plasma cell to a subject, such that the nucleic acid can be expressed in the subject in situ to provide a desired therapeutic effect. Suitable gene therapy and nucleic acid delivery vectors are known in the art.

Compositions of the invention may be immunogenic compositions, and in some embodiments may be vaccine compositions comprising an antigen comprising an epitope recognized by an antibody of the invention. Vaccines according to the invention may either be prophylactic (i.e. to prevent infection) or therapeutic (i.e. to treat infection). In one embodiment, the invention provides a vaccine comprising a polypeptide comprising the amino acid sequence of SEQ ID NOs: 37, 38, 39 or 40. In another embodiment, the invention provides a vaccine comprising a polypeptide comprising the amino acid residues in the HA1 and HA2 polypeptides of one or two HA monomers as described above. The HA monomers can be uncleaved or cleaved.

Compositions may include an antimicrobial, particularly if packaged in a multiple dose format. They may comprise detergent e.g. a Tween (polysorbate), such as Tween 80. Detergents are generally present at low levels e.g. <0.01%. Compositions may also include sodium salts (e.g. sodium chloride) to give tonicity. A concentration of 10+2 mg/ml NaCl is typical.

Further, compositions may comprise a sugar alcohol (e.g. mannitol) or a disaccharide (e.g. sucrose or trehalose) e.g., at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

The compositions of the invention may also comprise one or more immunoregulatory agents. In one embodiment, one or more of the immunoregulatory agents include(s) an adjuvant.

The epitope compositions of the invention may elicit both a cell mediated immune response as well as a humoral immune response in order to effectively address influenza A virus infection. This immune response may induce long lasting (e.g., neutralizing) antibodies and a cell mediated immunity that can quickly respond upon exposure to influenza A virus.

Medical Treatments and Uses

The antibodies and antibody fragments of the invention or derivatives and variants thereof may be used for the treatment of influenza A virus infection, for the prevention of influenza A virus infection or for the diagnosis of influenza A virus infection.

Methods of diagnosis may include contacting an antibody or an antibody fragment with a sample. Such samples may be tissue samples taken from, for example, nasal passages, sinus cavities, salivary glands, lung, liver, pancreas, kidney, ear, eye, placenta, alimentary tract, heart, ovaries, pituitary, adrenals, thyroid, brain or skin. The methods of diagnosis may also include the detection of an antigen/antibody complex.

The invention therefore provides (i) an antibody, an antibody fragment, or variants and derivatives thereof according to the invention, (ii) an immortalized B cell clone according to the invention, (iii) an epitope capable of binding an antibody of the invention or (iv) a ligand, preferably an antibody, capable of binding an epitope that binds an antibody of the invention for use in therapy.

The invention also provides a method of treating a subject comprising administering to the subject an antibody, an antibody fragment, or variants and derivatives thereof according to the invention, or, a ligand, preferably an antibody, capable of binding an epitope that binds an antibody of the invention. In one embodiment, the method results in reduced influenza A virus infection in the subject. In another embodiment, the method prevents, reduces the risk or delays influenza A virus infection in the subject.

The invention also provides the use of (i) an antibody, an antibody fragment, or variants and derivatives thereof according to the invention, (ii) an immortalized B cell clone according to the invention, (iii) an epitope capable of binding an antibody of the invention, or (iv) a ligand, preferably an antibody, that binds to an epitope capable of binding an antibody of the invention, in the manufacture of a medicament for the prevention or treatment of influenza A virus infection.

The invention provides a composition of the invention for use as a medicament for the prevention or treatment of a influenza A virus infection. It also provides the use of an antibody of the invention and/or a protein comprising an epitope to which such an antibody binds in the manufacture of a medicament for treatment of a subject and/or diagnosis in a subject. It also provides a method for treating a subject, comprising the step of administering to the subject a composition of the invention. In some embodiments the subject may be a human. One way of checking efficacy of therapeutic treatment involves monitoring disease symptoms after administration of the composition of the invention. Treatment can be a single dose schedule or a multiple dose schedule.

In one embodiment, an antibody, antibody fragment, immortalized B cell clone, epitope or composition according to the invention is administered to a subject in need of such treatment. Such a subject includes, but is not limited to, one who is particularly at risk of or susceptible to influenza A virus infection, including, for example, an immunocompromised subject. The antibody or antibody fragment of the invention can also be used in passive immunisation or active vaccination.

Antibodies and fragments thereof as described in the present invention may also be used in a kit for the diagnosis of influenza A virus infection. Further, epitopes capable of binding an antibody of the invention may be used in a kit for monitoring the efficacy of vaccination procedures by detecting the presence of protective anti-influenza A virus antibodies. Antibodies, antibody fragment, or variants and derivatives thereof, as described in the present invention may also be used in a kit for monitoring vaccine manufacture with the desired immunogenicity.

The invention also provides a method of preparing a pharmaceutical, comprising the step of admixing a monoclonal antibody with one or more pharmaceutically-acceptable carriers, wherein the monoclonal antibody is a monoclonal antibody that was obtained from a transfected host cell of the invention. Thus the procedures for first obtaining the monoclonal antibody (e.g. expressing it and/or purifying it) and then admixing it with the pharmaceutical carrier(s) can be performed at very different times by different people in different places (e.g. in different countries).

Starting with a transformed B cell or a cultured plasma cell of the invention, various steps of culturing, sub-culturing, cloning, sub-cloning, sequencing, nucleic acid preparation etc. can be performed in order to perpetuate the antibody expressed by the transformed B cell or the cultured plasma cell, with optional optimization at each step. In a preferred embodiment, the above methods further comprise techniques of optimization (e.g. affinity maturation or optimization) applied to the nucleic acids encoding the antibody. The invention encompasses all cells, nucleic acids, vectors, sequences, antibodies etc. used and prepared during such steps.

In all these methods, the nucleic acid used in the expression host may be manipulated to insert, delete or amend certain nucleic acid sequences. Changes from such manipulation include, but are not limited to, changes to introduce restriction sites, to amend codon usage, to add or optimise transcription and/or translation regulatory sequences, etc. It is also possible to change the nucleic acid to alter the encoded amino acids. For example, it may be useful to introduce one or more (e.g. 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g. labels) or can introduce tags (e.g. for purification purposes). Mutations can be introduced in specific sites or can be introduced at random, followed by selection (e.g. molecular evolution). For instance, one or more nucleic acids encoding any of the CDR regions, heavy chain variable regions or light chain variable regions of antibodies of the invention can be randomly or directionally mutated to introduce different properties in the encoded amino acids. Such changes can be the result of an iterative process wherein initial changes are retained and new changes at other nucleotide positions are introduced. Moreover, changes achieved in independent steps may be combined. Different properties introduced into the encoded amino acids may include, but are not limited to, enhanced affinity.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x+10%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a subject or patient is intended to include prevention, prophylaxis and therapy. The terms "subject" or "patient" are used interchangeably herein to mean all mammals including humans. Examples of subjects include humans, cows, dogs, cats, horses, goats, sheep, pigs, and rabbits. In one embodiment, the patient is a human.

EXAMPLES

Exemplary embodiments of the present invention are provided in the following examples. The following examples are presented only by way of illustration and to assist one of ordinary skill in using the invention. The examples are not intended in any way to otherwise limit the scope of the invention.

Example 1

Generation and Characterization of Influenza A Virus Broadly Neutralizing Antibodies from Plasma Cells To identify individuals that may produce heterosubtypic antibodies in responses to the seasonal influenza vaccine (containing H1 and H3 HAs), we screened by ELISPOT circulating plasma cells collected on day 7 after boost for their capacity to secrete antibodies that bound to vaccine or to an unrelated H5 HA (A/VN/1203/04). Strikingly, while in four of the five donors tested H5-specific plasma cells were undetectable, in one donor 14% of IgG-secreting plasma cells produced antibodies to H5, while 57% produced antibodies to the vaccine. CD138+ plasma cells were isolated from peripheral blood mononuclear cells (PBMCs) collected 7 days after vaccination using magnetic micro-beads followed by cell-sorting using a FACSAria machine. Limiting numbers of plasma cells were seeded in microwell culture plates. The culture supernatants were tested in three parallel ELISAs using as antigens recombinant H5 or H9 HAs and the irrelevant antigen tetanus toxoid. Out of the 4,928 culture supernatants screened, 12 bound to H5 but not H9 HA, 25 to H9 but not H5 HA and 54 to both H5 and H9. Some of the 54 cultures with highest OD signal were subjected to RT-PCR and two paired VH and VL genes were retrieved.

The VH and VL genes were cloned into expression vectors and recombinant antibodies were produced by transfecting HEK293T cells. The two monoclonal antibodies, FI6 variant 2 and FI28, shared most V, D and J gene fragments (IGHV3-30*01, IGHD3-9*01, IGHJ4*02 and IGKV4-1*01), but differed in the N regions, in the IGKJ usage and in the pattern of somatic mutations and were therefore not clonally related.

The specificity of recombinant antibodies was investigated by ELISA using a panel of HAs belonging to different subtypes. Remarkably, FI6 bound all influenza A HA subtypes tested including group 1 (H1, H5 and H9) and group 2 (H3 and H7), while it did not bind HA from influenza B virus. In contrast FI28 bound only to the three group 1 HA (H1, H5 and H9).

TABLE 4

| | Binding to HA by ELISA (% of subtype specific control antibodies) | | | | |
|---|---|---|---|---|---|
| | H1 A/NC/ 20/99 | H3 A/BR/ 10/07 | H5 A/VN/ 1203/04 | H7 A/NL/ 219/03 | H9 A/HK/ 1073/99 |
| FI6 variant 2 | 85.9 | 68.5 | 73.7 | 87.9 | 98.7 |
| FI28 variant 1 | 59.4 | 1.3 | 46.3 | −0.5 | 87.7 |

Given the homology of VH and VL sequences of the two antibodies, shuffling experiments were performed using H and L chains of FI6 variant 2, FI28 variant 1, and 7I13, a hCMV-specific antibody that uses the same V, D and J elements of the H chain. While binding to H7 required the pairing of FI6 variant 2 H and L chains, binding to H5 was maintained when the FI6 variant 2 and FI28 variant 1 L chains were shuffled. In addition H5 binding was also observed when the H chain of FI6 variant 2 was paired to the unrelated 7I13 L chain. In contrast H5 binding was not observed when the homologous 7I13 H chain was paired with FI6 variant 2 L chain. Without being bound by any particular theory, these results suggest that the main contribution to H5 binding is from the H chain, while H7 binding requires a precise pairing between H and L chains of FI6 variant 2.

FI6 variant 2 and FI28 variant 1 were then tested for their capacity to neutralize group 1 and group 2 influenza A subtypes using pseudotyped viruses (Table 5) as well as infectious viruses (Table 6). Remarkably FI6 variant 2 neutralized all pseudoviruses tested, including six H5 isolates belonging to the antigenically divergent clades 0, 1, 2.1, 2.2 and 2.3, and two H7 avian isolates. In addition FI6 variant 2 neutralized all infectious viruses tested, including two H3N2 viruses and four H1N1 viruses spanning several decades, up to the recent H1N1 pandemic isolate A/CA/04/09 (Table 6). FI28 variant 1 neutralized all H5 pseudoviruses but did not neutralize H7 pseudoviruses as well as all the infectious viruses tested. The neutralizing titers on pseudoviruses were higher than titers on infectious viruses.

TABLE 5

| | Neutralization of HA-pseudotypes (IC90, µg/ml) | | | | | | | |
|---|---|---|---|---|---|---|---|---|
| | H5N1 | | | | | | H7N1 | |
| | A/HK/ 491/97 | A/HK/ 213/ 03 | A/VN/ 1203/ 04 | A/INDO/ 5/05 | A/WS/ MONG/ 05 | A/AH/ 1/05 | A/ck/IT/ 13474/ 99 | A/ck/FPV/ Ro/34 |
| FI6 variant 2 | 0.07 | 0.02 | 0.02 | 0.31 | 0.03 | 0.05 | 1.87 | 0.09 |
| FI28 variant 1 | 0.05 | 0.33 | 0.02 | 0.35 | 0.04 | 0.05 | >100 | >100 |

TABLE 6

| | Neutralization of infectious viruses (IC50, μg/ml) | | | | | |
|---|---|---|---|---|---|---|
| | H1N1 | | | | H3N2 | |
| | A/PR/ 8/34 | A/NC/ 20/99 | A/SI/ 3/06 | A/CA/ 4/09 | A/CA/ 7/04 | A/WI/ 67/05 |
| FI6 variant 2 | 2.2 | 6.3 | 8.8 | 12.5 | 7.9 | 12.5 |
| FI28 variant 1 | >100 | >100 | >100 | nd | >100 | >100 | nd, not done

Example 2

FI6 Variant 2 and FI28 Variant 1 Antigenic Binding Sites

To identify the antigenic sites to which the antibodies FI6 variant 2 and FI28 variant 1 bind, we first tested their capacity to inhibit binding of C179, a mouse monoclonal antibody that was mapped to a conserved region of the HA stem region (Y. Okuno, et al., *J Virol* 67, 2552 (1993)). Both FI6 variant 2 and FI28 variant 1 completely inhibited binding of C179 to recombinant H5 VN/1203/04 HA, indicating that they recognize an overlapping epitope. In contrast, FI6 variant 2 and FI28 variant 1 did not compete with a panel of H5-specific antibodies isolated from H5N1 immune donors that recognize different epitopes in the globular head of the HA (C. P. Simmons et al., PLoS Med 4, e178 (2007); S. Khurana et al., PLoS Med 6, e1000049 (2009)). Attempts to map the FI6 variant 2 epitope by selection of escape mutants failed, suggesting that its epitope cannot be easily mutated without compromising viral fitness.

We next performed peptide-based mapping using libraries of linear and cyclised peptides of HA A/VN/1194/04 as well as helix-scan using the systems of Pepscan Presto BV (Lelystad, The Netherlands). This analysis identified a binding region of FI6 variant 2 that includes the HA2 fusion peptide FGAIAG (amino acid 3-8, according to H3 numbering; SEQ ID NO: 37), the HA2 Helix A peptide DGVTNKVNS (amino acid 46-54; SEQ ID NO: 38), the HA2 Helix B peptide MENERTLDFHDSNVK (amino acid 102-116; SEQ ID NO: 39) and the HA1 C-terminal peptide LVLATGLRNSP (amino acid 315-325; SEQ ID NO: 40). The binding region of FI28 variant 1 was different from that of FI6 since this antibody did not react with the HA1 C-terminal peptide and the HA2 Helix B peptide.

Example 3

Generation and Characterization of FI6 Variants 3, 4 and 5 with Improved Productivity Several variants of FI6 variant 2 VH and VL were synthesized to improve production in mammalian cells and to remove unnecessary somatic mutations and unwanted features. The VH and VL genes were cloned into expression vectors encoding the constant region of IgG1 and Cκ, respectively. Germline sequences of FI6 variant 2 was determined with reference to the IMGT database. Antibody variants in which single or multiple germline mutations were reverted to the germline were produced either by synthesis (Genscript, Piscatawy, N.J.) or by site directed mutagenesis (Promega) and confirmed by sequencing. All variant sequences were codon optimized for expression in human cells using the GenScript's OptimumGene™ system. Monoclonal antibodies were produced by transient transfection of suspension cultured 293 Freestyle cells (Invitrogen) with PEI. Supernatants from transfected cells were collected after 7 days of culture and IgG were affinity purified by Protein A chromatography (GE Healthcare) and desalted against PBS. Productivity in transient expression system was evaluated in several independent experiments. Mean values are shown in FIG. 1. As shown in FIG. 1, FI6 variant 2 is produced at a titer of 13.5 μg/ml; FI6 variant 3 is produced at a titer of 46.3 μg/ml; FI6 variant 4 is produced at a titer of 60.7 μg/ml; and FI6 variant 5 is produced at a titer of 61.6 μg/ml. Thus, we were able to achieve a 3.4-, 4.5- and 4.6-fold increase in titers of production of FI6 variants 3, 4 and 5, respectively, as compared to FI6 variant 2.

The recombinant antibodies were also characterized for binding by ELISA to H5 and H7 HAs and neutralization of H5 and H7 pseudoviruses (Table 7) compared to the original FI6 variant 2 IgG. Half-area ELISA plates (Corning) were coated with 5 μl of 1 μg/ml baculovirus-derived recombinant HAs (Protein Sciences Corp.) in PBS. After blocking with 1% PBS/BSA, antibodies were added and the binding was revealed using alkaline-phosphatase conjugated F(ab')2 goat anti human IgG (Southern Biotech). Plates were then washed, substrate (p-NPP, Sigma) was added and plates were read at 405 nm. The relative affinities of antibody binding to HAs were determined with ELISA by measuring the concentration of antibody required to achieve 50% maximal binding (EC50). For pseudovirus neutralization assays, serial dilutions of antibody were incubated with a fixed concentration pseudovirus-containing culture supernatants for 1 hour at 37° C. The mixtures were then added to HEK 293T/17 cells and incubated for 3 days at 37° C. The cells were then lysed with Britelite reagent (Perkin Elmer) and the relative light units (RLU) in the cell lysates were determined on a luminometer microplate reader (Veritas, Turner Biosystems). The reduction of infectivity was determined by comparing the RLU in the presence and absence of antibodies and expressed as percent neutralization. The 50% inhibitory dose (IC50) was defined as the sample concentration at which RLU were reduced 50% compared to virus control wells after subtraction of background RLU in cell only control wells. Table 7 shows the FI6 variants 3-5 that were selected based on improved sequence characteristics combined with preserved or improved binding activity.

TABLE 7

| | Binding | | Neutralization | |
|---|---|---|---|---|
| | | | H5 A/VN/ | H7 A/ck/FPV |
| mAb ID | H5-HA EC$_{50}$ (μg/ml) | H7-HA EC$_{50}$ (μg/ml) | 1194/04 IC50 (μg/ml) | Rostock/34 IC50 (μg/ml) |
| FI6 variant 2 | 0.0145 | 0.0314 | 0.0054 | 0.0200 |
| FI6 variant 3 | 0.0235 | 0.0573 | 0.0035 | 0.0274 |
| FI6 variant 4 | 0.0137 | 0.0267 | 0.0035 | 0.0093 |
| FI6 variant 5 | 0.0165 | 0.0473 | 0.0054 | 0.0220 |

FI6 variant 2 and FI6 variant 3 bound all recombinant or purified HAs tested belonging to Group 1 (H1, H2, H5, H6, H8 and H9) and Group 2 (H3, H4, H7 and H10) with EC50 values ranging from 10 to 270 ng/ml (Table 8). In addition, FI6 variant 2 and FI6 variant 3 stained cells transfected with HA genes belonging to Group 1 (H11, H12, H13 and H16) and Group 2 (H4, H10, H14 and H15 (Table 8).

TABLE 8

| HA protein | FI6 variant 2 | FI6 variant 3 | ctr |
|---|---|---|---|
| H1N1 A/Solomon Islands/3/06 | 18[1] | 19[1] | >20000[1] |
| H1N1 A/New Caledonia/20/99 | 15 | 17 | >20000 |
| H1N1 A/California/04/09 | 17 | 17 | >20000 |
| H1N1 A/Brisbane/59/07 | 15 | 17 | >20000 |
| H3N2 A/Wyoming/3/03 | 19 | 23 | >20000 |
| H3N2 A/New York/55/04 | 32 | 38 | >20000 |
| H3N2 A/Brisbane/10/07 | 41 | 37 | >20000 |
| H5N1 A/Viet Nam/1203/04 | 14 | 14 | >20000 |
| H5N1 A/Viet Nam/1/05 | 10 | 11 | >20000 |
| H7N7 A/Netherlands/219/03 | 26 | 29 | >20000 |
| H9N2 A/Hong Kong/1073/03 | 14 | 15 | >20000 |
| H4N6 A/duck/Czechoslovakia/56 | 273 | 185 | >20000 |
| H6N5 A/shearwater/Australia/1/72 | 41 | 34 | >20000 |
| H7N3 A/Canada/444/04 | 33 | 25 | >20000 |
| H8N4 A/Alberta/357/84 | 33 | 27 | >20000 |
| H10N4 A/mink/Sweded/3900/84 | 90 | 85 | >20000 |
| H13N6 A/gull/Maryland/704/77 | 88 | 62 | >20000 |
| H2N2 A/Singapore/1/57 | 29 | 21 | >20000 |
| H11N9 A/duck/Memphis/546/74 | +[2] | +[2] | — |
| H12N5 A/duck/Alberta/60/76 | +[2] | +[2] | — |
| H13N6 A/gull/Maryland/704/77 | +[2] | +[2] | — |
| H16N3 A/black-headed gull/Sweded/2/99 | +[2] | +[2] | — |
| H4N6 A/duck/Czechoslovakia/56 | +[2] | +[2] | — |
| H10N7 A/chicken/Germany/N49 | +[2] | +[2] | — |
| H14N5 A/mallard/Astrakhan/263/82 | +[2] | +[2] | — |
| H15N9 A/shearwater/West Australia/2576/79 | +[2] | +[2] | — |
| B/Ohio/1/05 | >20000 | >20000 | >20000 |

[1] EC50 values (ng/ml) as measured by ELISA
[2] + refers to positive staining of HA-transfected 293 cells

Example 4

Structural Characterization of FI6 Variant 3 Epitopes on H1 and H3 HA

To identify the epitope recognized by FI6 variant 3 on Group 1 and Group 2 HAs and to describe the molecular interactions between the antibody and its target antigen, we crystallized complexes of FI6 variant 3 Fab fragment with H1 (Group 1) and H3 (Group 2) HA homotrimers. For crystallisation of FI6 variant 3/H1 homotrimeric HA complex, the ectodomain of H1 HA0 was expressed in Sf9 insect cells. cDNA corresponding to residues 11-329 (HA1) and 1-176 (HA2) (based on H3 numbering) was cloned into a BioFocus expression vector incorporating the GP67 secretion signal to allow secretion of expressed protein into the culture medium. The cloned cDNA was fused to a C-terminal trimerizing foldon sequence to allow for the formation of the trimeric form of H1 HA0. A thrombin cleavage sequence was included between the foldon sequence and the C terminus of HA2 to allow for removal of the foldon tag prior to crystallization and a 6-His tag was incorporated at the extreme C-terminus of the expressed polypeptide sequence for use in affinity purification.

Sf9 insect cells were infected with recombinant baculovirus and the 6-His tagged H1 HA0 was recovered from the culture medium by passage over Ni-NTA resin (Qiagen) and gel filtration (S200 column). Eluted protein corresponding to trimeric H1 HA0 was concentrated to 1 mg/ml before removal of the C-terminal tag by treatment with thrombin (5 units thrombin per mg HA0) for two hours at 20° C. Purified cleaved protein H1 HA0 was finally fractionated on a Mono Q anion exchange column. To allow for the formation of its complex with Fab-FI6 variant 3, purified H1 HA0 at between 0.5 and 1 mg/ml was mixed with a two-fold molar excess of purified Fab-FI6 variant 3. The complex was allowed to form by incubation at 4° C. for three hours before separation from excess Fab-FI6 variant 3 by fractionation on an S200 gel filtration column.

The purified complex of Fab-FI6 variant 3 and trimeric unprocessed H1 HA0 was concentrated to 12 mg/ml for use in crystallization. Crystals of the complex of Fab-FI6 variant 3 and H1 HA0 were grown in hanging drops by vapour diffusion over a well solution consisting of 0.1 M Bis Tris propane pH 7.0, 2.2 M ammonium sulfate. Crystals grew at 20° C. over a period of four weeks and were harvested from the drop into a 1:1 mix of well solution and 3.4 M sodium malonate pH 7.0 for cryo-protection before flash freezing in liquid nitrogen. The data set was collected at the Diamond Light Source, beam line IO3, and was indexed, integrated, and scaled using MOSFLM and SCALA, respectively.

Statistical analysis of the unit cell parameters and protein molecular weights suggested one haemagglutinin monomer and one Fab fragment per asymmetric unit; therefore, molecular replacement was performed using search models in their monomeric states. Initial phases were obtained using coordinates of monomeric H1 HA (PDB ID 1RD8) as the search model with the CCP4 program PHASER. Using the automated model fitting program FFFEAR, the variable domain of the heavy chain was successfully fitted into density and subsequent comparison with HA-antibody structures 3FKU and 3 GBN allowed placement of the light chain variable domain. Alternating rounds of model building and refinement were performed using COOT and REFMAC5, respectively. This was repeated until as much of the electron density map was fitted as possible and R-work and R-free values had leveled out.

Amino acids in the final PDB file are numbered following the Kabat convention. The final model contains all of the H1 HA and the heavy and light chain variable domains. For crystallization of FI6 variant 3/H3 heterotrimeric HA complexes, X-31 (H3N2) virus and the bromelain released HA (BHA) were purified and the Fab fragments were prepared by papain digestion. The FI6 variant 3 Fab was purified using Protein A sepharose affinity chromatography (HiTrap Protein A HP, 1 ml) followed by an S-200 size exclusion column. 3.5 mg of Fab were mixed with 3 mg of X-31 BHA and incubated at 4° C. overnight for complex formation and the complex was purified using a superose 6 SEC column. Peak fractions corresponding to the Fab-HA complex were pooled and concentrated for crystallization.

FI6 variant 3-H3 complex crystals were grown by vapour diffusion in sitting drops dispensed by an Oryx-6 crystallization robot from Douglas Instruments. Crystals were cryo-protected by the addition of 25% glycerol to the reservoir solution. The data set was collected at the Diamond Light Source, beam line IO3, and was indexed, integrated, and scaled using Denzo and Scalepack. The crystals, containing one H3 HA trimer complexed with three FI6 variant 3 Fabs in the asymmetric unit, were solved by molecular replacement using Amore. The molecular replacement calculations were done using the coordinates for the 2 Å structure of H3 HA trimer, the heavy and light chain variable domains of FI6 variant 3 from the FI6 variant 3/H1 complex and the constant domains (PDB ID 3HC0.pdb) as independent search objects. The molecular replacement solution was refined with Refmac5 and Pheonix interspersed with rounds of manual adjustments using Coot. Electron density maps were substantially improved by non-crystallographic averaging using DM.

Figure 2:
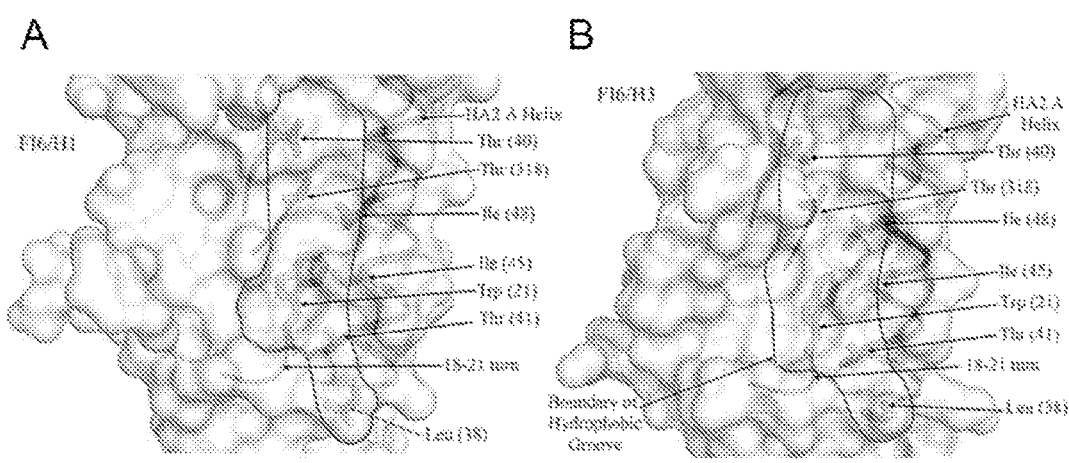
FIGS. 2A and 2B are surface representations of the F subdomain of H1 HA and H3 HA, respectively, in complex with FI6 variant 3 (referred to in the figure as FI6). The selected side-chains in HA1 and HA2 that contribute to the conserved hydrophobic groove are indicated by the arrows, the approximate boundaries of which are indicated by the black line. Thr (40) and Thr (318) are in HAL and Be (45), Trp (21), Thr (41), Leu (38) and the 18-21 turn are in HA2.
Figure 3:
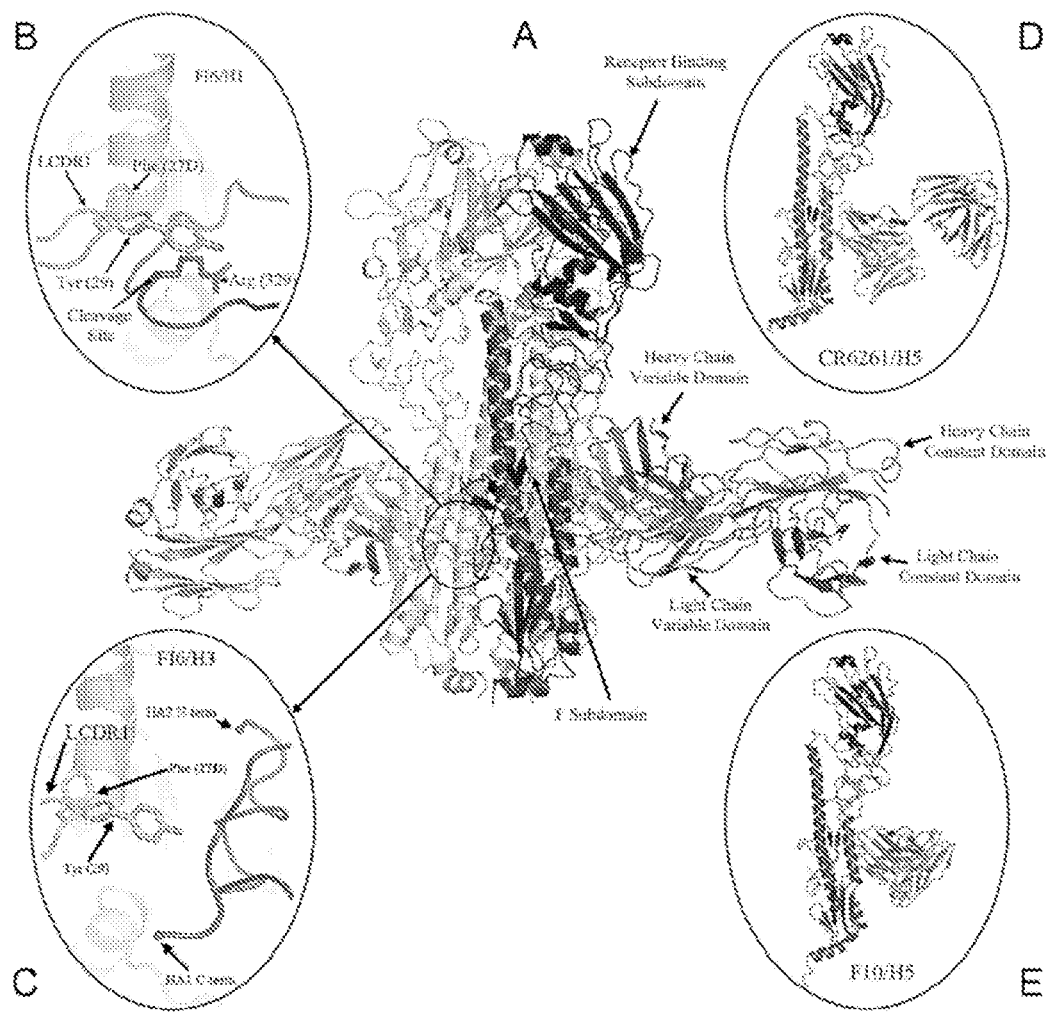
FIG. 3 shows the binding of FI6 variant 3 (referred to in the figure as FI6) to the F subdomain of the HA trimer.

X-ray crystallography showed that FI6 variant 3 bound to a conserved epitope in the F subdomain. Although the two HAs are phylogenetically and structurally distinct, and the complexes crystallize with different packing arrangements, the interaction surfaces were found to be very similar (FIGS. 2, A and B). In both cases, each monomer of the HA trimer binds one molecule of FI6 variant 3 (FIG. 3). The HCDR3 loop of FI6 variant 3 binds into a shallow groove on the F subdomain of the HAs where the sides of the groove are formed by residues from the A helix of HA2, and parts of two strands of HA1 (38-42 and 318-320), whereas the bottom is formed by the HA2 turn encompassing residues 18-21 (FIGS. 2, A and B).

Figure 4:
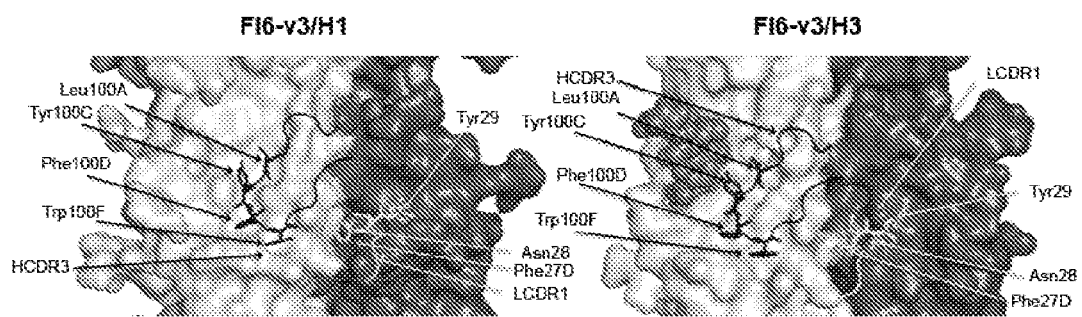
FIG. 4 shows the interactions of FI6 variant 3 (referred to in the figure as FI6-v3) with the F sub-domain of H1 and H3 HA. It depicts a surface representation of the F subdomain of H1 HA and H3 HA with the HCDR3 and LCDR1 loops of FI6 variant 3 with selected side chains. The proximal HA monomer is depicted in light grey; the distal right monomer is depicted in light grey; and the glycan bound to N38 of H3 HA1 is depicted as dark grey spheres.

The HCDR3 loop crosses helix A, at an angle of about 45°, enabling Leu-100A, Tyr-100C, Phe-100D, and Trp-100F to make hydrophobic contacts with residues in the groove (FIG. 4). Tyr-100C and Trp-100F also make potential hydrogen bonds with the side chain of Thr-318 of HA1 and the main chain carbonyl of residue 19 of HAL respectively. Two additional polar interactions are formed by main chain carbonyls at residues 98 and 99 of HCDR3 with Asn-53 and Thr-49 on helix A. Taken together the interaction of HCDR3 with HA (H1 and H3) buries about 750 Å2 of the surface of the antibody and about ⅔ of this interaction is accounted for by the interaction with the HA2 chain.

Overall, the interactions made by FI6 variant 3 with the hydrophobic groove on H1 and H3 are remarkably similar. The LCDR1 loop of FI6 variant 3 makes two contacts with the side of helix A, opposite to the side that contributes to the hydrophobic groove; Phe-27D makes hydrophobic contact with the aliphatic part of Lys-39 and Asn-28 hydrogen bonds to Asn-43, together accounting for a buried surface area of about 190 A2 for both H1 and H3. With H1 HA, which was co-crystallized in the un-cleaved form, LCDR1 also makes extensive contact with the un-cleaved "fusion peptide" of the neighboring distal right HA monomer (FIGS. 3, B and C and FIGS. 4, A and B), which amounts to an additional 320 A2 of FI6 variant 3 buried surface.

Residues 28 and 29 of LCDR1 make main chain amide hydrogen bonds with the main chain carbonyls of HA1 residue 329 and the next but one residue, Leu-2, of HA2, thus spanning the cleavage site. Phe-27D of LCDR1 makes hydrophobic contacts with Leu-2 of the neighboring distal right HA2, while the side chain hydroxyl of Tyr-29 hydrogen bonds to the main chain carbonyl of residue 325 of the neighboring distal right HA1 chain. In contrast to the very similar interaction between both H1 and H3 HAs with HCDR3, the interaction of LCDR1 with the "fusion peptide" from the neighboring cleaved distal right H3 HA monomer is significantly less extensive than the interaction formed with the un-cleaved H1 HA (FIG. 3, insert B). Although Phe-27D again makes contact with the aliphatic moiety of Lys-39 of HA2, Tyr-29 makes potential hydrogen bond contact with the main chain carbonyl of Ala-7 of the neighboring distal right HA2 (as opposed to residue 329 in un-cleaved H1 HA).

In contrast, there are no main chain contacts between the LCDR1 loop and the "fusion peptide" of the cleaved H3 HA, accounting for the smaller contact area of 114 Å (cf 320 Å2 in H1 HA). It also seems that cleavage of the HA precursor to produce the H3 HA, results in the slightly different orientation of FI6 variant 3 with respect to the HA in the FI6 variant 3/H3 and FI6 variant 3/H1 complexes. The contact residues at the interface between FI6 variant 3 VH and VL chains and cleaved H3 homotrimeric HA are reported in Table 9. The contact residues at the interface between FI6 variant 3 VH and VL chains and uncleaved H1 homotrimeric HA are reported in Table 10.

TABLE 9

Contact Residues at the Interface Between FI6 Variant 3 VH and VL and Cleaved H3-HA Trimer

| H3 | HA1 | | | | | | | | | | HA2 | | | |
|---|---|---|---|---|---|---|---|---|---|---|---|---|---|---|
| | Cleavage site - Fusion peptide | | | | | | | | | | Trp-21 loop | | | |
| HK68 | T318 | R321' | V323' | Q327' | S328' | R329' | G1' | L2' | F3' | G4' | A7' | E11' | I18 | D19 | G20 | W21 |
| FI6 v3 VH | Y100c | | | | | | | | | | | | F100d W100f | F100d | F100d | F100d |
| FI6 v3 VK | | N28 Y29 | Y29 | | | | | | | | Y29 | Y29 Y32 | | | | |

| H3 | | | | | HA2 Helix A | | | | | | | | |
|---|---|---|---|---|---|---|---|---|---|---|---|---|---|
| HK68 | L38 | K39 | T41 | Q42 | A43 | I45 | D46 | I48 | N49 | L52 | N53 | I56 | E57 |
| FI6 v3 VH | W100f | | W100f | W100f L100g S100h | L100b Y100c L100g | | | | L98 R99 S100 L100a | Y52a | L98 | | R99 S100 |
| FI6 v3 VK | R93 | F27d | | F27d | | | | | F27d Y32 | | | | | |

TABLE 10

Contact Residues at the Interface Between FI6 Variant 3 VH and VL and Uncleaved H1-HA Trimer

| | HA1 | | | | | | | | | | | | HA2 | | | |
|---|---|---|---|---|---|---|---|---|---|---|---|---|---|---|---|---|
| H1 | Cleavage site - Fusion peptide | | | | | | | | | | | | Trp-21 loop | | | |
| CA09 | T318 | R321' | I323' | Q327' | S328' | R329' | G1' | L2' | F3' | G4' | A7' | E11' | V18 | D19 | G20 | W21 |
| FI6 v3 VH | Y100c | | | | | | | | | | | | F100d | F100d W100f | F100d | Y100c F100d |
| FI6 v3 VK | | | Y29 | Y29 | T27c F27d N28 Y29 | T27c | S27a T27c F27d N28 Y92 | F27d | F27d | | | | | | | |

| | | | | | | HA2 Helix A | | | | | | | |
|---|---|---|---|---|---|---|---|---|---|---|---|---|---|
| H1 | | | | | | | | | | | | | |
| CA09 | L38 | K39 | T41 | Q42 | N43 | I45 | D46 | I48 | T49 | V52 | N53 | I56 | E57 |
| FI6 v3 VH | W100f | | W100f | W100f L100g S100h | | L100a Y100c L100g | | L100a | R99 L100a | | L98 R99 | R99 | L98 R99 |
| FI6 v3 VK | R93 | F27d | | | F27d N28 | | | | | | | | |

The structures of two cross-reactive antibodies CR6261 and F10, which are Group 1 specific, have previously been reported as complexes with H5 and H1 HAs. The CR6261 and F10 antibodies binding to HA is mediated only by their VH domains which are oriented approximately the same as each other with respect to the HA, but both antibodies are significantly rotated relative to FI6 variant 3 and are 5-10 Å nearer to the membrane proximal end of HA (FIGS. 3, D and E).

The structures of FI6 variant 3/H1 and FI6 variant 3/H3 presented here also reveal that, although the binding sites on HA of the three antibodies overlap extensively, the nature of the interactions made by FI6 variant 3 are markedly different to those made by CR6261 and F10 antibodies. The most striking difference is that the interaction of FI6 variant 3 with the hydrophobic groove on HA is mediated solely by the long HCDR3, whereas for CR6261 and F10 all three HCDRs are involved in binding.

An important difference between the FI6 variant 3/H1 and FI6 variant 3/H3 complexes is that H3 HA is glycosylated at Asn-38 (HA1), as are H7, H10 and H15 HAs of Group 2, while H1, in common with all Group 1 HAs is not. In the unbound structure of H3, this carbohydrate side-chain projects from the beta strand of HA1 that contains the Asn-38 residue, towards helix A of HA2 of the same HA subunit, such that it would overlap the footprint of FI6 variant 3 (FIG. 5A). Carbohydrate side-chains are known to influence the antigenicity of virus glycoproteins, therefore this overlap has been suggested to account for the lack of binding to Group 2 HAs of other Group 1 cross-reactive antibodies that target the membrane proximal region of HA. FI6 variant 3 binding to H3 HA, however, is enabled by reorientation of the oligosaccharide, a rotation of about 80° away from the surface of the HA, so that it makes new contacts with Asp-53 and Asn-55 of the HCDR2 loop (FIG. 5B).

Given that the flexibility of the carbohydrate side chain at Asn-38 allows it to accommodate FI6 variant 3 binding to H3 HA, we asked whether this glycosylation site was likely to be the reason that H3 HA does not bind to CR6261 or F10. Simple modeling suggests that the same change in orientation of the carbohydrate side-chain would be compatible with the binding of the CR6261, but not the F10, cross-reactive antibodies. The beta turn encompassing VH residues 73-77 of F10 would clash with the Asn-38-linked carbohydrate in the orientation it adopts in the FI6 variant 3/H3 complex, and it is unclear whether the carbohydrate would be free to rotate further out of the binding site to accommodate F10 binding. However, neither CR6261 nor F10 were able to neutralize a H7 pseudovirus (A/chicken/Italy/99) in which the glycosylation site (Asn-38) was removed (IC50>50 µg/ml), indicating that the steric hindrance of the glycan is not the only structural constraint that prevents binding of CR6261 and F10 antibodies to Group 2 HAs.

Figure 5:
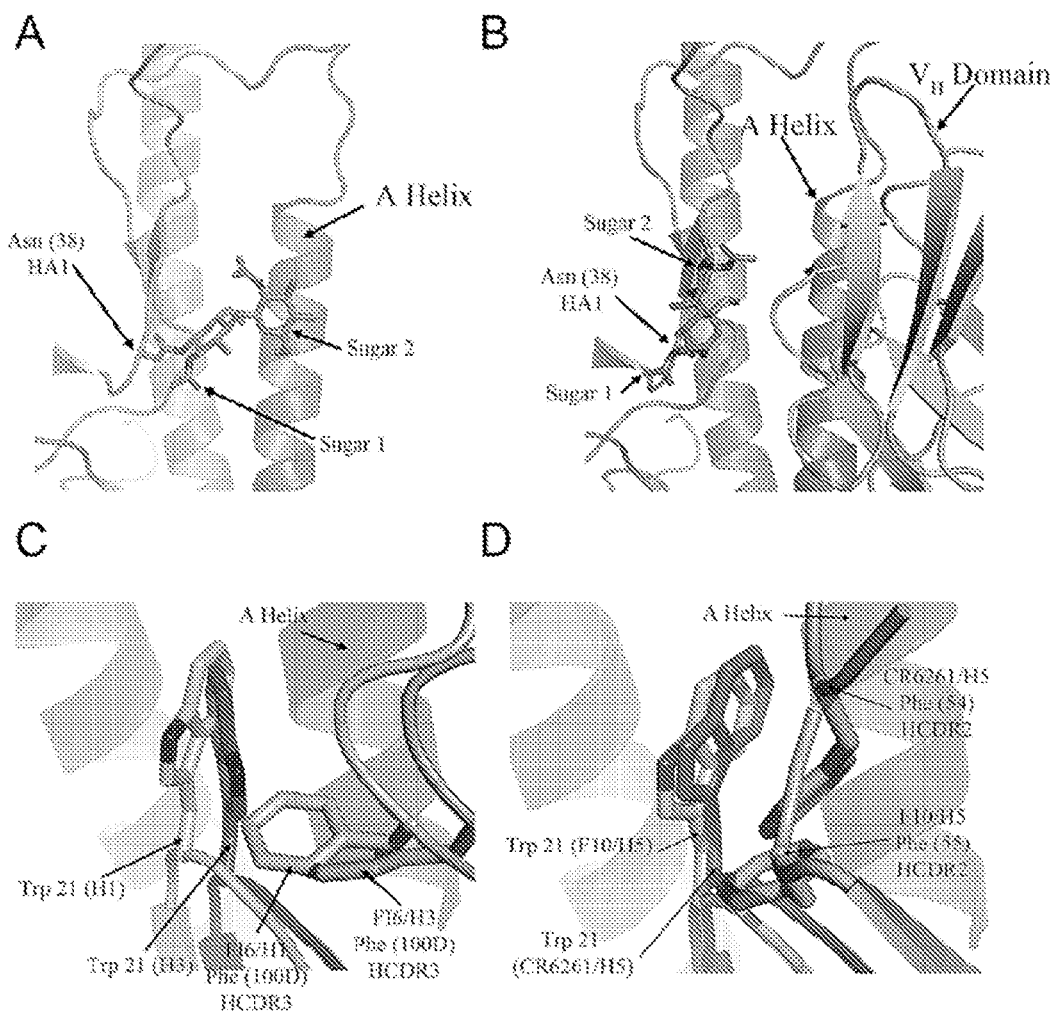
FIG. 5 shows group-specific differences at the cross-reactive antibody binding sites.

Besides the glycosylation of Asn-38 the most striking difference in the F subdomain structure between Group 1 and Group 2 HAs involves the Group-distinctive environment and orientation of HA2 Trp-21. In Group-1 HAs, Trp-21 is approximately parallel to the surface of the F subdomain, while in Group-2 HAs it is oriented roughly perpendicular to the surface (FIGS. 5, C and D). All three antibodies (FI6 variant 3, CR6261 and F10) make contacts with Trp-21, mainly through a phenylalanine side chain; Phe-100D on FI6 variant 3, Phe-54 on CR6261 and Phe-55 on F10 (FIGS. 5, C and D). In the case of FI6 variant 3, local rearrangements in the HCDR3 loop mean that Phe-100D sits approximately 2 Å deeper in the hydrophobic groove in the H1 complex than it does in the H3 complex; it thus maintains a similar contact distance with Trp-21 in both cases.

The two Group-1 specific antibodies position Phe-54 (CR6261) and Phe-55 (F10) similarly to FI6 variant 3 in complex with H1 HA. However, as Phe-54 (CR6261) and Phe-55 (F10) are located on the short loop HCDR2, which connects two adjacent anti-parallel strands, it seems that there is less flexibility than in FI6 variant 3 for the phenylalanine to move further out of the hydrophobic groove to accommodate the Group-2 orientation of Trp-21. Thus, binding of CR6261 and F10 to Group 2 HAs is likely blocked by a steric clash between the HCDR2 phenylalanine and Trp-21.

Figure 6:
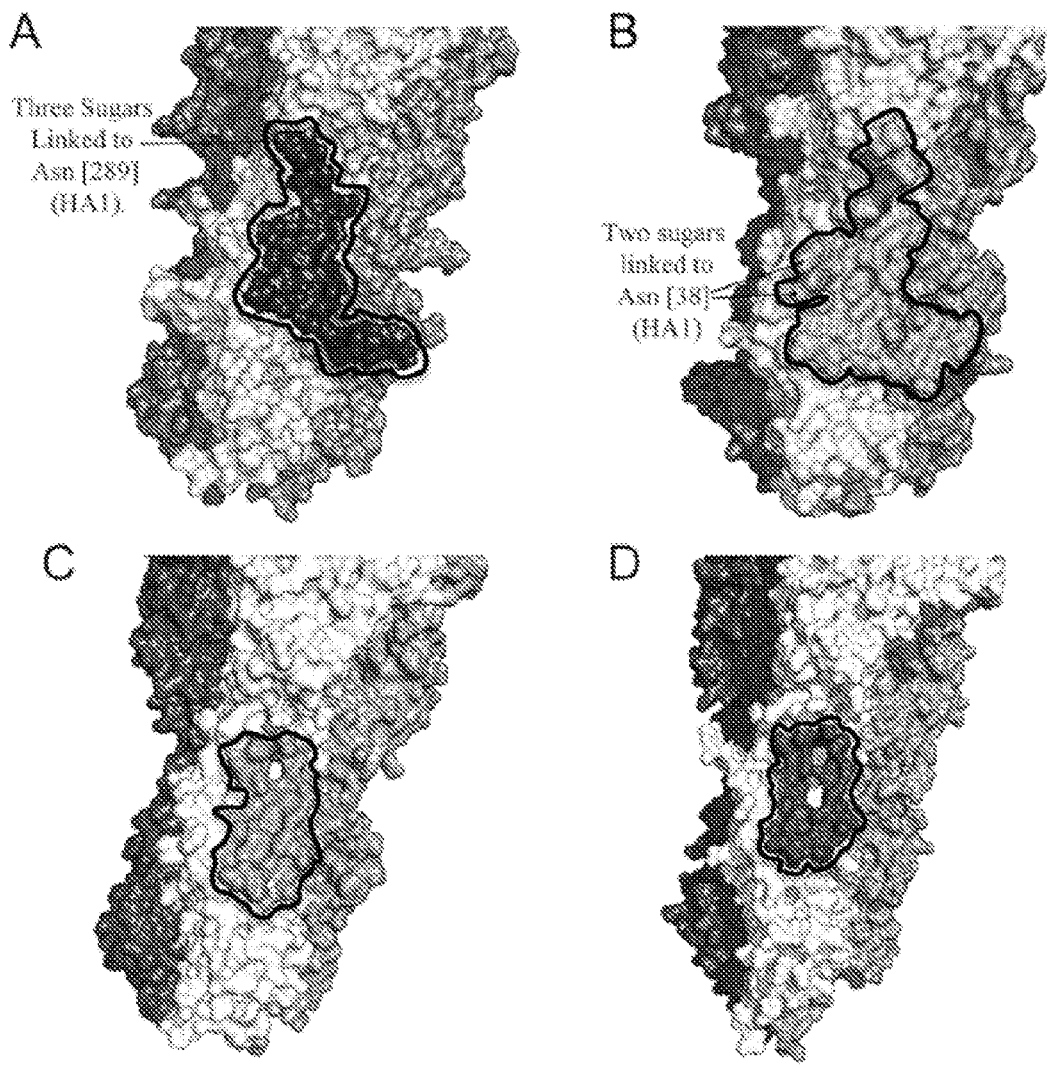
FIG. 6 shows the contact surface of FI6 variant 3 on HA. The four panels show the footprints (contoured with a black line) on HA of FI6 variant 3, CR6261 and F10 antibodies; the three HA monomers are depicted as white, light or dark grey.

In summary, the structural data obtained indicate that, although the core epitope on helix A is similar to that recognized by CR6261 and F10, FI6 variant 3 binds with a different angle, 5-10 Å more membrane distal and contacts a larger area embracing helix A and extending to the fusion peptide of the neighboring distal right monomer both in the cleaved and uncleaved forms (FIG. 6). FI6 variant 3 binding is mediated by both VH and VL CDRs, with prominent contributions of the long HCDR3, which accommodates different conformations of the Group-specific Trp-21 loop, and of the heavily mutated LCDR1. The use of both VH and VK chains and the long HCDR3 are characteristic of naturally selected antibodies and contrast with the property of phage-derived antibodies, such as CR6261 and F10, which bind using only the VH chain. The contact residues in FI6 variant 3 VH and VK are depicted in FIG. 7.

Example 5

In Vivo Prophylactic Effect of FI6 Variant 3

The protective efficacy of FI6 variant 3 was tested in vivo in mouse models of Influenza A virus infection. Groups of 6- to 8-week-old female BALB/c mice were injected intravenously (i.v.) with purified antibodies at concentrations varying from 1 to 16 mg/kg. Three hours later, the mice were deeply anaesthetized and challenged intranasally (i.n.) with 10 MLD50 (fifty percent mouse lethal dose) of H1N1 A/PR/8/34. In a therapeutic setting, mice received the antibody 1, 2 or 3 days after infection. The mice were monitored daily for survival and weight loss until day 14 post-infection (p.i.). Animals that lost more than 25% of their initial body weight were euthanized in accordance with animal study protocol.

Figure 8:
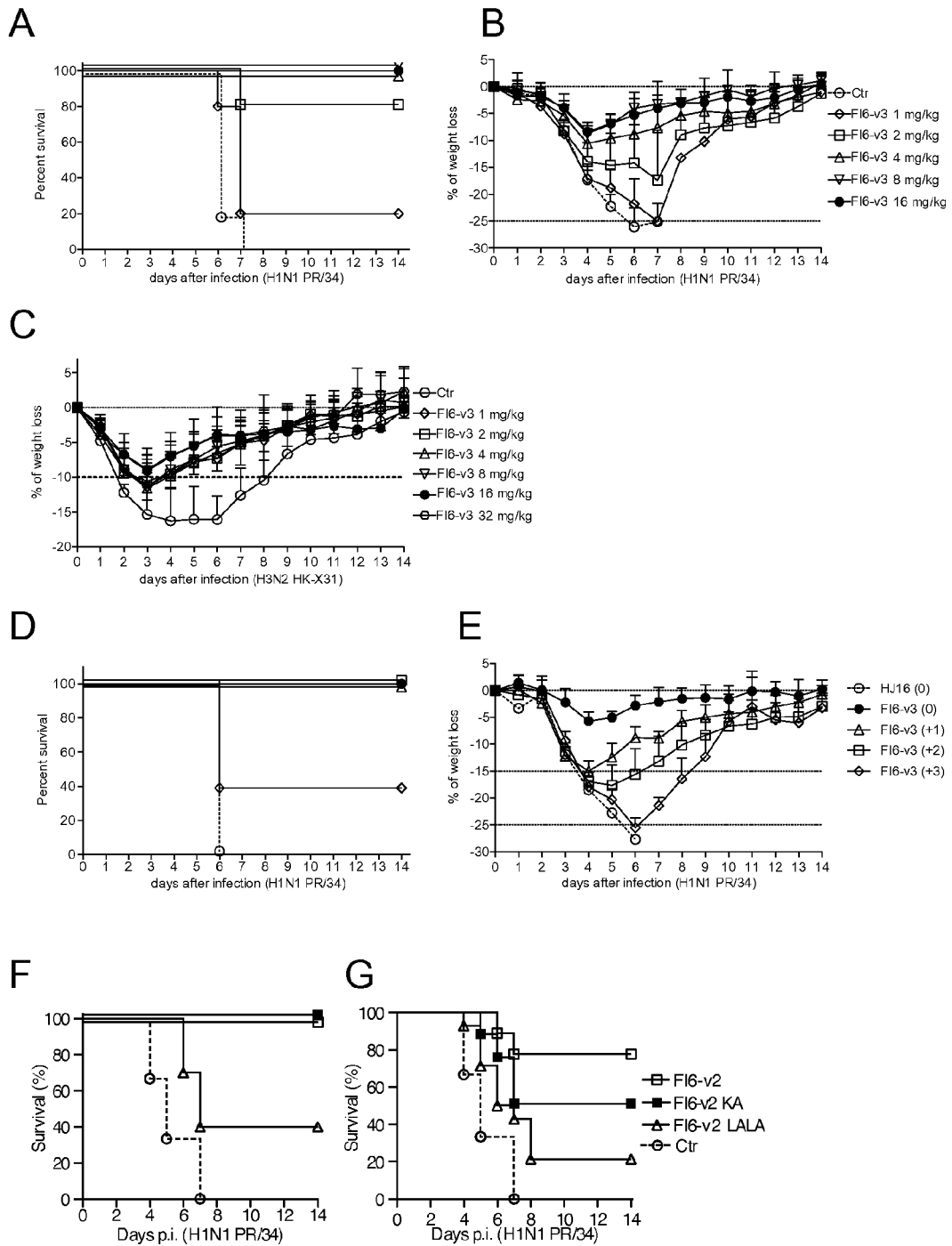
FIG. 8 shows that FI6 variant 3 confers protection in mouse models of Influenza A virus infection.
Figure 9:
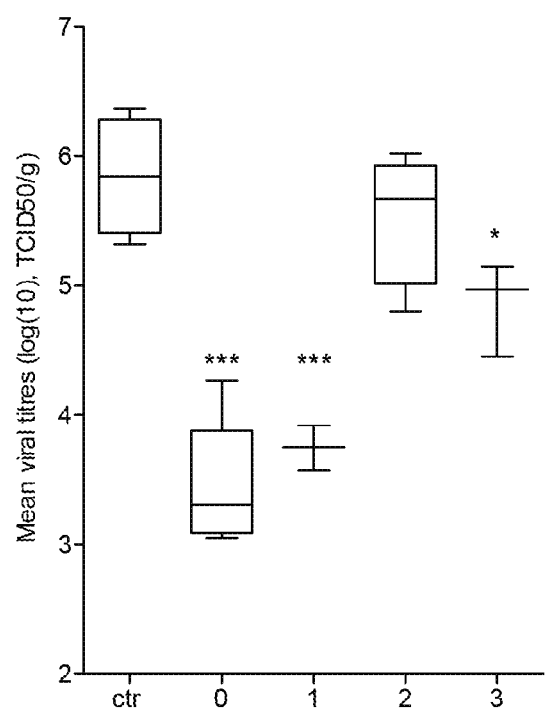
FIG. 9 shows pulmonary virus titers of mice treated with FI6 variant 3 after H1N1 PR/8/34 lethal challenge. BALB/c mice (four mice per experimental condition) received i.v. injection of 15 mg/kg FI6 variant 3 or a control antibody (HJ16, HIV-1 specific) three hours before (day 0) or 1, 2 or 3 days after i.n. infection with 10 MLD50 H1N1 PR/8/34. Viral titers were determined 4 days post infection in lungs. Virus was undetectable in the brains. Data are displayed in box-and-whiskers form in which the box extends from the 25th to the 75th percentile, with a horizontal line at the median. Whiskers above and below the box indicate the extreme values. Results of Students' t-test statistic analysis are noted as * for $p<0.05$, and as *** for $p<0.001$.

To evaluate the influence of FI6 variant 3 on viral replication, mice challenged with 10 MLD50 of H1N1 A/PR/8/34 received the antibody at different time points and were sacrificed four days later to collect lungs and brains. The tissues were homogenized in Leibovitz L-15 medium (Invitrogen) supplemented with an antibiotic-antimycotic solution (Invitrogen) to achieve 10% w/v organ suspension. The organ homogenates were titrated on MDCK cells and virus titers were determined. In a prophylactic setting FI6 variant 3 was fully protective and when administered at 4 mg/kg was partially protective (80% survival) when administered at 2 mg/kg to mice infected with Group 1 H1N1 A/PR/8/34 virus (FIG. 8). Lung virus titers at day four after infection were reduced by approximately a hundred fold in mice treated with FI6 variant 3 on day 0 or 1 day after infection (FIG. 9). In addition, FI6 variant 3 prevented body weigh loss of mice infected with Group 2 H3N2 HK-x31 virus (FIG. 8).

Example 6

Mechanisms of Virus Neutralization by FI6 Variant 3

For in vivo experiments aimed at determining the protective efficacy of FI6 antibodies, we produced Fc mutants of FI6 variant 2 that lack complement binding (FI6-v2 KA) or complement and FcR binding (FI6-v2 LALA). These antibodies showed the same binding and in vitro neutralizing properties as FI6 variant 2 and comparable half lives in vivo (mean values 3.3, 3.4 and 3.5 days for FI6-v2, FI6-v2 KA and FI6-v2 LALA, respectively). Their protective efficacy was tested in mice lethally infected with A/Puerto Rico/8/34 (H1N1) virus. FI6.v2 fully protected mice from lethality when administered at 4 mg/kg and protected 80% of mice at 2 mg/kg (FIG. 8F). When administered at 10 mg/kg, FI6-v2 and FI6-v2 KA were fully protective, whereas FI6-v2 LALA showed a substantial loss of activity, being able to protect only 40% of the animals (FIG. 8F). This decreased efficacy was particularly evident when mutant antibodies were administered at the limiting concentration of 3 mg/kg (FIG. 8G).

To investigate mechanisms that contribute to the neutralizing activity of FI6 variant 3, NC/99 baculo-derived HA (Protein Sciences Corporation) were incubated for 40 minutes at 37° C. with a 15 times higher molar amounts FI6 variant 3, FE17, a non-specific mAb (HBD85) or no mAb in PBS solution. TPCK treated trypsin was added to each sample to a final concentration of 2.5 µg/ml and digestion was performed at 37° C. for 5, 10 and 20 minutes. At each time point, the digestion was stopped by adding a buffer containing SDS and DTT and by boiling it at 95° C. for 5 minutes. Samples were then loaded on a 12% Tris-Glycine polyacrylamide gel. Protein transfer on a PVDF membrane was performed with the iBlot blotting system from Invitrogen. PVDF membrane was blocked for 30 minutes with 10% non-fat dry milk in TBS-Tween. Incubation with primary antibody against HA0 (in house produced biotinylated FO32) was performed at 0.5 µg/ml in TBS-Tween overnight at 4° C. PVDF was washed three times with TBS-Tween and incubated for 1 h at RT with HRP-conjugated Streptavidin (Sigma).

Figure 10:
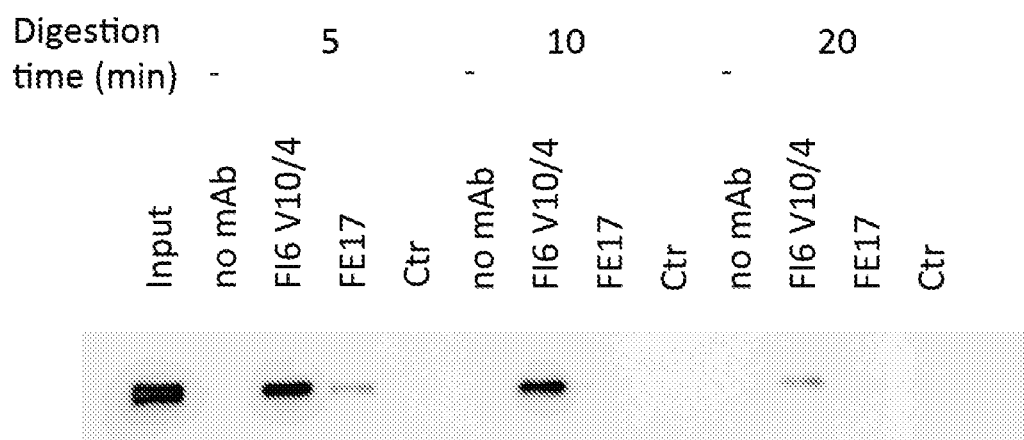
FIG. 10 shows that FI6 variant 3 binding to HA stem region interferes with protease-mediated HA0 cleavage. Recombinant HA from the H1 NC/99 isolate was incubated with FI6 variant 3, FE17 (a human antibody that recognizes the Ca2 site on the HA globular head) or a control antibody. The HA-antibody mixture was then exposed to TPCK-treated trypsin for 5, 10 or 20 minutes at 37° C. The samples were then run on a polyacrilamide gel and Western blots were developed using a biotinylated human mAb (FO32) that recognizes HA2 and HA0 of all influenza A strains under denaturing conditions. Shown is the HA0 band. One representative experiment out of three is shown.

PVDF membrane was washed three times with TBS-Tween and positive bands detected using ECL Plus™ Western Blotting Detection Reagent (GE Healthcare) and the LAS4000 CCD camera system. The data in FIG. 10 show that FI6 variant 3 inhibits cleavage of HA0 by TPCK-trypsin, indicating that the antibody light chain binding to unprocessed HA0 blocks infectivity, at least for those viruses where cleavage occurs extracellularly.

REFERENCES

Okuno et al., (1993) Journal of Virology 67: 2552
Gerhard et al., (2006) Emerging Infectious Diseases 12: 569
Gioia et al., (2008) Emerging Infectious Diseases 14: 121
U.S. Pat. No. 3,766,162
U.S. Pat. No. 3,791,932
U.S. Pat. No. 3,817,837
U.S. Pat. No. 4,233,402
U.S. Pat. No. 4,676,980
U.S. Pat. No. 4,831,175
U.S. Pat. No. 5,595,721
WO00/52031
WO00/52473
U.S. Pat. No. 4,766,106
U.S. Pat. No. 4,179,337
U.S. Pat. No. 4,495,285
U.S. Pat. No. 4,609,546
Gabizon et al., (1982) Cancer Research 42:4734
Cafiso (1981) Biochem Biophys Acta 649:129
Szoka (1980) Ann. Rev. Biophys. Eng. 9:467
Poznansky et al., (1980) Drug Delivery Systems (R. L. Juliano, ed., Oxford, N.Y.) pp. 253-315
Poznansky (1984) Pharm Revs 36:277
Kohler, G. and Milstein, C, 1975, Nature 256:495-497.
Kozbar et al., 1983, Immunology Today 4:72.
WO2004/076677

Chapter 4 of Kuby Immunology (4th edition, 2000; ASIN: 0716733315)
Jones et al., Biotechnol Prog 2003, 19(1):163-8
Cho et al., Cytotechnology 2001, 37:23-30
Cho et al., Biotechnol Prog 2003, 19:229-32
U.S. Pat. No. 5,807,715

U.S. Pat. No. 6,300,104
Rowe et al., (1999) J Clin Microbiol 37(4):937-43.
Temperton, et al., (2005). Emerg Infect Dis 11, 411-416.
Smirnov et al., (2000). Arch Virol 145, 1733-1741.
Smirnov et al., (1999). Acta Virol 43, 237-244.
Simmons et al., (2007). PLoS Med 4, e178.
Traggiai et al., (2004). Nat Med 10, 871-875.

The invention claimed is:

1. An isolated antibody, or an antigen-binding fragment thereof, that neutralizes infection of a group 1 subtype and a group 2 subtype of influenza A virus and comprises: (i) the heavy chain CDR1, CDR2 and CDR3 sequences as set forth in SEQ ID NOs: 1, 41 and 43, respectively, and the light chain CDR1, CDR2, and CDR3 sequences as set forth in SEQ ID NOs: 4, 5 and 6, respectively; or (ii) the heavy chain CDR1, CDR2 and CDR3 sequences as set forth in SEQ ID NOs: 1, 41 and 42, respectively, and the light chain CDR1, CDR2, and CDR3 sequences as set forth in SEQ ID NOs: 4, 5 and 6, respectively; or (iii) the heavy chain CDR1, CDR2 and CDR3 sequences as set forth in SEQ ID NOs: 1, 41 and 43, respectively, and the light chain CDR1, CDR2, and CDR3 sequences as set forth in SEQ ID NOs: 44, 5 and 6, respectively.

2. The antibody, or antigen binding fragment thereof, of claim 1, comprising a heavy chain variable region having at least 80% sequence identity to the amino acid sequence of SEQ ID NO: 59 and a light chain variable region having at least 80% sequence identity to the amino acid sequence of SEQ ID NO: 57; or a heavy chain variable region having at least 80% sequence identity to the amino acid sequence of SEQ ID NO: 59 and a light chain variable region having at least 80% sequence identity to the amino acid sequence of SEQ ID NO: 61; or a heavy chain variable region having at least 80% sequence identity to the amino acid sequence of SEQ ID NO: 55 and a light chain variable region having at least 80% sequence identity to the amino acid sequence of SEQ ID NO: 57; or a heavy chain variable region having at least 80% sequence identity to the amino acid sequence of SEQ ID NO: 55 and a light chain variable region having at least 80% sequence identity to the amino acid sequence of SEQ ID NO: 61.

3. An isolated antibody, or an antigen binding fragment thereof, that comprises a heavy chain variable region comprising the amino acid sequence of SEQ ID NO: 59 and a light chain variable region comprising the amino acid sequence of SEQ ID NO: 57; or a heavy chain variable region comprising the amino acid sequence of SEQ ID NO: 59 and a light chain variable region comprising the amino acid sequence of SEQ ID NO: 61; or a heavy chain variable region comprising the amino acid sequence of SEQ ID NO: 55 and a light chain variable region comprising the amino acid sequence of SEQ ID NO: 57; or a heavy chain variable region comprising the amino acid sequence of SEQ ID NO: 55 and a light chain variable region comprising the amino acid sequence of SEQ ID NO: 61 and wherein the antibody neutralizes a group 1 subtype and a group 2 subtype of influenza A virus.

4. The antibody, or antigen binding fragment thereof, of any one of claim 1, 2 or 3, wherein the antibody is a human antibody, a monoclonal antibody, a purified antibody, a single chain antibody, Fab, Fab', F(ab')2, Fv or scFv.

5. A recombinant nucleic acid molecule comprising a polynucleotide encoding the antibody, or an antigen binding fragment thereof, of claim 1.

6. The recombinant nucleic acid molecule of claim 5, wherein the polynucleotide comprises a sequence that is at least 75% identical to the nucleic acid sequence as set forth in any one of SEQ ID NOs: 45-54, 56, 58, 60 or 62.

7. The recombinant nucleic acid molecule of claim 5, wherein the polynucleotide comprises a sequence as set forth in SEQ ID NOs: 60 and 58; or SEQ ID NOs: 60 and 62; or SEQ ID NOs: 56 and 58; or SEQ ID NOs: 56 and 62.

8. A vector comprising a polynucleotide encoding the antibody, or an antigen binding fragment thereof, of claim 1.

9. An isolated recombinant cell expressing the antibody of claim 1, or an antigen binding fragment thereof; or comprising the vector of claim 8.

10. A pharmaceutical composition comprising the antibody of any one of claim 1, 2 or 3, or an antigen binding fragment thereof, a recombinant nucleic acid molecule comprising a polynucleotide encoding said antibody, or antigen binding fragment thereof; a vector comprising said polynucleotide; or a cell expressing said vector, and a pharmaceutically acceptable diluent or carrier.

11. A method of reducing influenza A virus infection, or lowering the risk of influenza A virus infection, comprising: administering to a subject in need thereof, a prophylactically or therapeutically effective amount of the antibody of any one of claim 1, 2 or 3, or an antigen binding fragment thereof.

* * * * *

SEQUENCE LISTING

```
<160> NUMBER OF SEQ ID NOS: 62

<210> SEQ ID NO 1
<211> LENGTH: 8
<212> TYPE: PRT
<213> ORGANISM: Homo sapiens

<400> SEQUENCE: 1

Gly Phe Thr Phe Ser Thr Tyr Ala
1               5

<210> SEQ ID NO 2
<211> LENGTH: 8
<212> TYPE: PRT
<213> ORGANISM: Homo sapiens

<400> SEQUENCE: 2

Ile Ser Tyr Asp Gly Asn Tyr Lys
1               5

<210> SEQ ID NO 3
<211> LENGTH: 22
<212> TYPE: PRT
<213> ORGANISM: Homo sapiens

<400> SEQUENCE: 3

Ala Lys Asp Ser Gln Leu Arg Ser Leu Leu Tyr Phe Glu Trp Leu Ser
1               5                   10                  15

Gln Gly Tyr Phe Asp Pro
            20

<210> SEQ ID NO 4
<211> LENGTH: 10
<212> TYPE: PRT
<213> ORGANISM: Homo sapiens

<400> SEQUENCE: 4

Gln Ser Val Thr Phe Asn Tyr Lys Asn Tyr
1               5                   10

<210> SEQ ID NO 5
<211> LENGTH: 3
<212> TYPE: PRT
<213> ORGANISM: Homo sapiens

<400> SEQUENCE: 5

Trp Ala Ser
1

<210> SEQ ID NO 6
<211> LENGTH: 9
<212> TYPE: PRT
<213> ORGANISM: Homo sapiens

<400> SEQUENCE: 6

Gln Gln His Tyr Arg Thr Pro Pro Thr
```

<210> SEQ ID NO 7
<211> LENGTH: 24
<212> TYPE: DNA
<213> ORGANISM: Homo sapiens

<400> SEQUENCE: 7
ggattcacgt tcagtaccta tgcc                                          24

<210> SEQ ID NO 8
<211> LENGTH: 24
<212> TYPE: DNA
<213> ORGANISM: Homo sapiens

<400> SEQUENCE: 8
atctcatacg atggaaatta taaa                                          24

<210> SEQ ID NO 9
<211> LENGTH: 66
<212> TYPE: DNA
<213> ORGANISM: Homo sapiens

<400> SEQUENCE: 9
gcgaaagact cccaactgcg atcactcctc tattttgaat ggttatccca gggatatttt   60
gacccc                                                              66

<210> SEQ ID NO 10
<211> LENGTH: 30
<212> TYPE: DNA
<213> ORGANISM: Homo sapiens

<400> SEQUENCE: 10
cagagtgtca ccttcaacta taagaactac                                    30

<210> SEQ ID NO 11
<211> LENGTH: 9
<212> TYPE: DNA
<213> ORGANISM: Homo sapiens

<400> SEQUENCE: 11 tgggcatct                                                            9

<210> SEQ ID NO 12
<211> LENGTH: 27
<212> TYPE: DNA
<213> ORGANISM: Homo sapiens

<400> SEQUENCE: 12
cagcaacatt ataggactcc tccgacg                                       27

<210> SEQ ID NO 13
<211> LENGTH: 129
<212> TYPE: PRT
<213> ORGANISM: Homo sapiens

<400> SEQUENCE: 13

Gln Val Gln Leu Val Gln Ser Gly Gly Gly Val Val Gln Pro Gly Arg
 1               5                  10                  15

Ser Leu Arg Leu Ser Cys Val Ala Ser Gly Phe Thr Phe Ser Thr Tyr
            20                  25                  30

Ala Met His Trp Val Arg Gln Ala Pro Gly Arg Gly Leu Glu Trp Val
            35                  40                  45

Ala Val Ile Ser Tyr Asp Gly Asn Tyr Lys Tyr Tyr Ala Asp Ser Val
 50                  55                  60

Lys Gly Arg Phe Ser Ile Ser Arg Asp Asn Ser Asn Ser Thr Leu His
65                  70                  75                  80

Leu Glu Met Asn Thr Leu Arg Thr Glu Asp Thr Ala Leu Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Pro Trp Gly Gln Gly Thr Leu Val Thr Val Thr
            115                 120                 125

Ser

<210> SEQ ID NO 14
<211> LENGTH: 111
<212> TYPE: PRT
<213> ORGANISM: Homo sapiens

<400> SEQUENCE: 14

Asp Ile Gln Met Thr Gln Ser Pro Asp Ser Leu Ala Val Ser Leu Gly
1               5                   10                  15

Ala Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
        35                  40                  45

Lys Val Leu Ile Tyr Trp Ala Ser Ala Arg Glu Ser Gly Val Pro Asp
 50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Thr Phe Gly Gln Gly Thr Lys Val Glu Ile Lys
            100                 105                 110

<210> SEQ ID NO 15
<211> LENGTH: 388
<212> TYPE: DNA
<213> ORGANISM: Homo sapiens

<400> SEQUENCE: 15
caggtgcagc tggtgcagtc tggggagggc gtggtccagc ctgggaggtc cctgagactc      60
tcctgtgtag cctctggatt cacgttcagt acctatgcca tgcactgggt ccgtcaggct     120
ccaggcaggg ggctggagtg ggtggcagtt atctcatacg atggaaatta taaatactat     180
gcagactctg tgaagggccg attctccatc tccagagaca attccaacag cacgctgcat     240
ctagaaatga acaccctgag aactgaggac acggctttat attactgtgc gaaagactcc     300
caactgcgat cactcctcta ttttgaatgg ttatcccagg gatattttga cccctggggc     360
cagggaaccc ttgtcaccgt cacctcag                                        388

<210> SEQ ID NO 16
<211> LENGTH: 334
<212> TYPE: DNA
<213> ORGANISM: Homo sapiens

<400> SEQUENCE: 16

```
gacatccaga tgacccagtc tccagactcc ctggctgtat ctctgggcgc gagggccacc      60
atcaactgca agtccagcca gagtgtcacc ttcaactata agaactactt agcttggtac     120
cagcagaaac caggacagcc tcctaaagtg ctcatttact gggcatctgc ccgggaatca     180
ggggtccctg accgattcag tggcagcggg tctgggacag atttcactct caccatcagc     240
agcctgcagg ctgaagatgt ggctgtttat tactgtcagc aacattatag gactcctccg     300
acgttcggcc aagggaccaa ggtggagatc aaac                                 334
```

<210> SEQ ID NO 17
<211> LENGTH: 8
<212> TYPE: PRT
<213> ORGANISM: Homo sapiens

<400> SEQUENCE: 17

Gly Phe Thr Phe Ser Asn Tyr Gly
1               5

<210> SEQ ID NO 18
<211> LENGTH: 8
<212> TYPE: PRT
<213> ORGANISM: Homo sapiens

<400> SEQUENCE: 18

Ile Ser Tyr Asp Gly Ser Asn Lys
1               5

<210> SEQ ID NO 19
<211> LENGTH: 22
<212> TYPE: PRT
<213> ORGANISM: Homo sapiens

<400> SEQUENCE: 19

Ala Lys Glu Arg Pro Leu Arg Leu Leu Arg Tyr Phe Asp Trp Leu Ser
1               5                   10                  15

Gly Gly Ala Asn Asp Tyr
            20

<210> SEQ ID NO 20
<211> LENGTH: 12
<212> TYPE: PRT
<213> ORGANISM: Homo sapiens

<400> SEQUENCE: 20

Gln Ser Val Leu Tyr Ser Ser Asn Asn Lys Asn Tyr
1               5                   10

<210> SEQ ID NO 21
<211> LENGTH: 3
<212> TYPE: PRT
<213> ORGANISM: Homo sapiens

<400> SEQUENCE: 21

Trp Ala Ser
1

<210> SEQ ID NO 22
<211> LENGTH: 8
<212> TYPE: PRT
<213> ORGANISM: Homo sapiens

```
<400> SEQUENCE: 22

Gln Gln Tyr Tyr Arg Ser Pro Ser
1               5

<210> SEQ ID NO 23
<211> LENGTH: 24
<212> TYPE: DNA
<213> ORGANISM: Homo sapiens

<400> SEQUENCE: 23
ggattcacct tcagtaacta tggc                                              24

<210> SEQ ID NO 24
<211> LENGTH: 24
<212> TYPE: DNA
<213> ORGANISM: Homo sapiens

<400> SEQUENCE: 24
atatcatatg atggatctaa taag                                              24

<210> SEQ ID NO 25
<211> LENGTH: 66
<212> TYPE: DNA
<213> ORGANISM: Homo sapiens

<400> SEQUENCE: 25
gcgaaagaga gaccccttcg cctattacga tattttgact ggttatcggg ggggcgaat        60 gactac                                                                  66

<210> SEQ ID NO 26
<211> LENGTH: 36
<212> TYPE: DNA
<213> ORGANISM: Homo sapiens

<400> SEQUENCE: 26
cagagtgttt tatacagctc caacaataag aactac                                 36

<210> SEQ ID NO 27
<211> LENGTH: 9
<212> TYPE: DNA
<213> ORGANISM: Homo sapiens

<400> SEQUENCE: 27 tgggcatct                                                               9

<210> SEQ ID NO 28
<211> LENGTH: 24
<212> TYPE: DNA
<213> ORGANISM: Homo sapiens

<400> SEQUENCE: 28
cagcagtatt atagaagtcc gtcc                                              24

<210> SEQ ID NO 29
<211> LENGTH: 129
<212> TYPE: PRT
<213> ORGANISM: Homo sapiens

<400> SEQUENCE: 29

Glu Val Gln Leu Val Glu Ser Gly Gly Gly Ala Val Gln Pro Gly Glu
1               5                   10                  15
```

Ser Leu Lys Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Leu Phe Tyr Cys
                85                  90                  95

Ala Lys Glu Arg Pro Leu Arg Leu Leu Arg Tyr Phe Asp Trp Leu Ser
            100                 105                 110

Gly Gly Ala Asn Asp Tyr Trp Gly Gln Gly Thr Leu Val Thr Val Ser
        115                 120                 125

Ser

<210> SEQ ID NO 30
<211> LENGTH: 112
<212> TYPE: PRT
<213> ORGANISM: Homo sapiens

<400> SEQUENCE: 30

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Asp Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Asn Leu Gln Val Glu Asp Val Ala Val Tyr Tyr Cys Gln Gln
                85                  90                  95

Tyr Tyr Arg Ser Pro Ser Phe Gly Gln Gly Thr Lys Leu Glu Ile Lys
            100                 105                 110

<210> SEQ ID NO 31
<211> LENGTH: 388
<212> TYPE: DNA
<213> ORGANISM: Homo sapiens

<400> SEQUENCE: 31
gaggtgcagc tggtggagtc tgggggaggc gcggtccagc ctggggagtc cctgaaactc    60
tcctgtgcag cctctggatt caccttcagt aactatggca tgcactgggt ccgccaggct   120
ccaggcaagg gactggagtg gtggcagtc atatcatatg atggatctaa taagtactat   180
gcagactccg tgaagggccg attcaccatc tccagagaca attccaagga cacgctgtat   240
ctgcaaatga acagcctgag agctgaggac acggctctgt tttactgtgc gaaagagaga   300
ccccttcgcc tattacgata ttttgactgg ttatcggggg gggcgaatga ctactggggc   360
cagggaaccc tggtcaccgt ctcctcag                                      388

<210> SEQ ID NO 32
<211> LENGTH: 337
<212> TYPE: DNA
<213> ORGANISM: Homo sapiens

<400> SEQUENCE: 32

```
gacatcgtga tgacccagtc tccagactcc ctggctgtgt ctctgggcga gagggccacc    60
atcaactgca agtccagcca gagtgtttta tacagctcca acaataagaa ctacttagct   120
tggtaccagc agaaaccagg acagcctcct aagttgctca ttgactgggc atctacccgg   180
gaatccgggg tccctgaccg attcagtggc agcgggtctg ggacagattt cactctcacc   240
atcagcaatc tgcaggttga agatgtggcc gtttattact gtcagcagta ttatagaagt   300
ccgtcctttg gcaggggac caagctggag atcaaac                             337
```

<210> SEQ ID NO 33
<211> LENGTH: 129
<212> TYPE: PRT
<213> ORGANISM: Homo sapiens

<400> SEQUENCE: 33

```
Gln Val Gln Leu Val Gln Ser Gly Gly Gly Val Val Gln Pro Gly Arg
 1               5                  10                  15
Ser Leu Arg Leu Ser Cys Val Ala Ser Gly Phe Thr Phe Ser Thr Tyr
            20                  25                  30
Ala Met His Trp Val Arg Gln Ala Pro Gly Arg Gly Leu Glu Trp Val
        35                  40                  45
Ala Val Ile Ser Tyr Asp Gly Asn Tyr Lys Tyr Ala Asp Ser Val
    50                  55                  60
Lys Gly Arg Phe Ser Ile Ser Arg Asp Asn Ser Asn Asn Thr Leu His
65                  70                  75                  80
Leu Glu Met Asn Thr Leu Arg Thr Glu Asp Thr Ala Leu Tyr Tyr Cys
                85                  90                  95
Ala Lys Asp Ser Gln Leu Arg Ser Leu Leu Tyr Phe Glu Trp Leu Ser
            100                 105                 110
Gln Gly Tyr Phe Asp Pro Trp Gly Gln Gly Thr Leu Val Thr Val Thr
        115                 120                 125
Ser
```

<210> SEQ ID NO 34
<211> LENGTH: 388
<212> TYPE: DNA
<213> ORGANISM: Homo sapiens

<400> SEQUENCE: 34

```
caggtgcagc tggtgcagtc tggggaggc gtggtccagc ctgggaggtc cctgagactc     60
tcctgtgtag cctctggatt cacgttcagt acctatgcca tgcactgggt ccgtcaggct   120
ccaggcaggg gctggagtg gtggcagtt atctcatacg atggaaatta taaatactat    180
gcagactctg tgaagggccg attctccatc tccagagaca attccaacaa cacgctgcat   240
ctagaaatga acaccctgag aactgaggac acggctttat attactgtgc gaaagactcc   300
caactgcgat cactcctcta ttttgaatgg ttatcccagg gatattttga cccctggggc   360
cagggaaccc tggtcaccgt cacctcag                                      388
```

<210> SEQ ID NO 35
<211> LENGTH: 129
<212> TYPE: PRT
<213> ORGANISM: Homo sapiens

<400> SEQUENCE: 35

Glu Val Gln Leu Val Glu Ser Gly Gly Ala Val Gln Pro Gly Glu
1               5                   10                  15

Ser Leu Lys Leu Pro Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Leu Phe Tyr Cys
                85                  90                  95

Ala Lys Glu Arg Pro Leu Arg Leu Arg Tyr Phe Asp Trp Leu Ser
            100                 105                 110

Gly Gly Ala Asn Asp Tyr Trp Gly Gln Gly Thr Leu Val Thr Val Ser
        115                 120                 125

Ser

<210> SEQ ID NO 36
<211> LENGTH: 388
<212> TYPE: DNA
<213> ORGANISM: Homo sapiens

<400> SEQUENCE: 36

```
gaggtgcagc tggtggagtc tgggggaggc gcggtccagc ctggggagtc cctgaaactc      60
ccctgtgcag cctctggatt caccttcagt aactatggca tgcactgggt ccgccaggct     120
ccaggcaagg gactggagtg gtggcagtc atatcatatg atggatctaa taagtactat      180
gcagactccg tgaagggccg attcaccatc tccagagaca attccaagga cacgctgtat     240
ctgcaaatga acagcctgag agctgaggac acggctctgt tttactgtgc gaaagagaga     300
ccccttcgcc tattacgata ttttgactgg ttatcggggg gggcgaatga ctactggggc     360
cagggaaccc tggtcaccgt ctcctcag                                        388
```

<210> SEQ ID NO 37
<211> LENGTH: 6
<212> TYPE: PRT
<213> ORGANISM: Homo sapiens

<400> SEQUENCE: 37

Phe Gly Ala Ile Ala Gly
1               5

<210> SEQ ID NO 38
<211> LENGTH: 9
<212> TYPE: PRT
<213> ORGANISM: Homo sapiens

<400> SEQUENCE: 38

Asp Gly Val Thr Asn Lys Val Asn Ser
1               5

<210> SEQ ID NO 39
<211> LENGTH: 15
<212> TYPE: PRT
<213> ORGANISM: Homo sapiens

<400> SEQUENCE: 39

Met Glu Asn Glu Arg Thr Leu Asp Phe His Asp Ser Asn Val Lys
1               5                   10                  15

<210> SEQ ID NO 40
<211> LENGTH: 11
<212> TYPE: PRT
<213> ORGANISM: Homo sapiens

<400> SEQUENCE: 40

Leu Val Leu Ala Thr Gly Leu Arg Asn Ser Pro
1               5                   10

<210> SEQ ID NO 41
<211> LENGTH: 8
<212> TYPE: PRT
<213> ORGANISM: Homo sapiens

<400> SEQUENCE: 41

Ile Ser Tyr Asp Ala Asn Tyr Lys
1               5

<210> SEQ ID NO 42
<211> LENGTH: 22
<212> TYPE: PRT
<213> ORGANISM: Homo sapiens

<400> SEQUENCE: 42

Ala Lys Asp Ser Gln Leu Arg Ser Leu Leu Tyr Phe Glu Trp Leu Ser
1               5                   10                  15

Gln Gly Tyr Phe Asp Tyr
            20

<210> SEQ ID NO 43
<211> LENGTH: 22
<212> TYPE: PRT
<213> ORGANISM: Homo sapiens

<400> SEQUENCE: 43

Ala Lys Asp Ser Gln Leu Arg Ser Leu Leu Tyr Phe Glu Trp Leu Ser
1               5                   10                  15

Gln Gly Tyr Phe Glu Pro
            20

<210> SEQ ID NO 44
<211> LENGTH: 10
<212> TYPE: PRT
<213> ORGANISM: Homo sapiens

<400> SEQUENCE: 44

Gln Ser Val Thr Phe Asn Asn Lys Asn Tyr
1               5                   10

<210> SEQ ID NO 45
<211> LENGTH: 24
<212> TYPE: DNA
<213> ORGANISM: Homo sapiens

<400> SEQUENCE: 45
ggattcacct tttctacata cgct                                        24

<210> SEQ ID NO 46
<211> LENGTH: 24
<212> TYPE: DNA

<213> ORGANISM: Homo sapiens

<400> SEQUENCE: 46
atctcatacg acgctaacta taag                                        24

<210> SEQ ID NO 47
<211> LENGTH: 66
<212> TYPE: DNA
<213> ORGANISM: Homo sapiens

<400> SEQUENCE: 47
gccaaagatt ctcagctgag gagtctgctg tatttcgaat ggctgagcca ggggtacttt    60
gattat                                                              66

<210> SEQ ID NO 48
<211> LENGTH: 30
<212> TYPE: DNA
<213> ORGANISM: Homo sapiens

<400> SEQUENCE: 48
cagtctgtga ctttcaacta caaaaattat                                   30

<210> SEQ ID NO 49
<211> LENGTH: 9
<212> TYPE: DNA
<213> ORGANISM: Homo sapiens

<400> SEQUENCE: 49 tgggcttca                                                           9

<210> SEQ ID NO 50
<211> LENGTH: 27
<212> TYPE: DNA
<213> ORGANISM: Homo sapiens

<400> SEQUENCE: 50
cagcagcact accggactcc acccacc                                       27

<210> SEQ ID NO 51
<211> LENGTH: 24
<212> TYPE: DNA
<213> ORGANISM: Homo sapiens

<400> SEQUENCE: 51
ggattcactt tttccaccta cgca                                          24

<210> SEQ ID NO 52
<211> LENGTH: 24
<212> TYPE: DNA
<213> ORGANISM: Homo sapiens

<400> SEQUENCE: 52
atctcatacg acgccaacta taag                                          24

<210> SEQ ID NO 53
<211> LENGTH: 66
<212> TYPE: DNA
<213> ORGANISM: Homo sapiens

<400> SEQUENCE: 53
gctaaggatt ctcagctgag aagtctgctg tattttgaat ggctgtctca ggggtatttt    60
gaacct                                                              66

<210> SEQ ID NO 54
<211> LENGTH: 30
<212> TYPE: DNA
<213> ORGANISM: Homo sapiens

<400> SEQUENCE: 54
cagtctgtga ctttcaacaa caaaaattat         30

<210> SEQ ID NO 55
<211> LENGTH: 129
<212> TYPE: PRT
<213> ORGANISM: Homo sapiens

<400> SEQUENCE: 55

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser

<210> SEQ ID NO 56
<211> LENGTH: 387
<212> TYPE: DNA
<213> ORGANISM: Homo sapiens

<400> SEQUENCE: 56
caggtgcagc tggtggagtc cggaggagga gtggtgcagc cagggcggtc tctgagactg         60
agttgcgccg cttcaggatt cacctttct acatacgcta tgcactgggt gcggcaggct        120
cctggcaagg gactggaatg ggtggccgtg atctcatacg acgctaacta taagtactat        180
gccgatagcg tgaaaggcag gttcacaatt agccgcgaca actccaagaa tactctgtac        240
ctgcagatga attccctgag ggctgaggac accgccgtgt actattgtgc caaagattct        300
cagctgagga gtctgctgta tttcgaatgg ctgagccagg ggtactttga ttattgggga        360
cagggcactc tggtgaccgt gagctcc                                            387

<210> SEQ ID NO 57
<211> LENGTH: 111
<212> TYPE: PRT
<213> ORGANISM: Homo sapiens

<400> SEQUENCE: 57

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
                35                  40                  45

Lys Leu Leu Ile Tyr Trp Ala Ser Thr Arg Glu Ser Gly Val Pro Asp
 50                      55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Tyr
                 85                  90                  95

Arg Thr Pro Pro Thr Phe Gly Gln Gly Thr Lys Val Glu Ile Lys
             100                 105                 110

<210> SEQ ID NO 58
<211> LENGTH: 333
<212> TYPE: DNA
<213> ORGANISM: Homo sapiens

<400> SEQUENCE: 58
gacatcgtga tgactcagtc tcccgatagt ctggccgtgt ccctgggcga gagggctaca      60
attaactgca agagctccca gtctgtgact ttcaactaca aaattatct ggcctggtac     120 cagcagaagc ctggacagcc ccctaaactg ctgatctatt gggcttcaac ccgggaaagc     180
ggcgtgccag acagattctc aggcagcggg tccggaacag acttcaccct gacaatttct     240
agtctgcagg ccgaggacgt ggccgtgtac tattgtcagc agcactaccg gactccaccc     300 accttggcc aggggacaaa ggtggaaatc aaa                                   333

<210> SEQ ID NO 59
<211> LENGTH: 129
<212> TYPE: PRT
<213> ORGANISM: Homo sapiens

<400> SEQUENCE: 59

Gln Val Gln Leu Val Gln Ser Gly Gly Gly Val Val Gln Pro Gly Arg
 1               5                  10                  15

Ser Leu Arg Leu Ser Cys Val Ala Ser Gly Phe Thr Phe Ser Thr Tyr
            20                  25                  30

Ala Met His Trp Val Arg Gln Ala Pro Gly Arg Gly Leu Glu Trp Val
        35                  40                  45

Ala Val Ile Ser Tyr Asp Ala Asn Tyr Lys Tyr Tyr Ala Asp Ser Val
 50                  55                  60

Lys Gly Arg Phe Ser Ile Ser Arg Asp Asn Ser Gln Asn Thr Leu His
 65                  70                  75                  80

Leu Glu Met Asn Thr Leu Arg Thr Glu Asp Thr Ala Leu Tyr Tyr Cys
                 85                  90                  95

Ala Lys Asp Ser Gln Leu Arg Ser Leu Leu Tyr Phe Glu Trp Leu Ser
            100                 105                 110

Gln Gly Tyr Phe Glu Pro Trp Gly Gln Gly Thr Leu Val Thr Val Thr
        115                 120                 125

Ser

<210> SEQ ID NO 60
<211> LENGTH: 387
<212> TYPE: DNA
<213> ORGANISM: Homo sapiens

<400> SEQUENCE: 60

-continued

```
caggtccagc tggtccagag cggcggcggc gtggtccagc cagggaggtc actgagactg      60
tcatgcgtcg cttcaggatt cactttttcc acctacgcaa tgcactgggt gcggcaggca     120
cctggaagag gactggagtg ggtggcagtc atctcatacg acgccaacta taagtactat     180
gctgatagcg tcaaaggcag gttcagcatt tcccgcgaca acagtcagaa tacactgcat     240
ctggagatga ataccctgcg aacagaagac actgccctgt actattgcgc taaggattct     300
cagctgagaa gtctgctgta ttttgaatgg ctgtctcagg ggtattttga accttggggg     360
cagggcactc tggtcaccgt cacttcc                                         387

<210> SEQ ID NO 61
<211> LENGTH: 111
<212> TYPE: PRT
<213> ORGANISM: Homo sapiens

<400> SEQUENCE: 61

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Asn
            20                  25                  30

Asn Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Thr Phe Gly Gln Gly Thr Lys Val Glu Ile Lys
            100                 105                 110

<210> SEQ ID NO 62
<211> LENGTH: 333
<212> TYPE: DNA
<213> ORGANISM: Homo sapiens

<400> SEQUENCE: 62
gacatcgtga tgactcagtc tcccgatagt ctggccgtgt ccctgggcga gagggctaca      60
attaactgca agagctccca gtctgtgact ttcaacaaca aaaattatct ggcctggtac     120
cagcagaagc ctggacagcc ccctaaactg ctgatctatt gggcttcaac ccgggaaagc     180
ggcgtgccag acagattctc aggcagcggg tccggaacag acttcaccct gacaatttct     240
agtctgcagg ccgaggacgt ggccgtgtac tattgtcagc agcactaccg gactccaccc     300
acctttggcc aggggacaaa ggtggaaatc aaa                                  333
```